(12) United States Patent
Nizin et al.

(10) Patent No.: US 8,125,813 B2
(45) Date of Patent: Feb. 28, 2012

(54) VARIANCE REDUCTION SIMULATION SYSTEM, PROGRAM PRODUCT, AND RELATED METHODS

(75) Inventors: Paul S. Nizin, Sugar Land, TX (US); Feng Ma, Houston, TX (US); Ramiro Pino, Pearland, TX (US)

(73) Assignee: Best Medical International, Inc., Springfield, VA (US)

( * ) Notice: Subject to any disclaimer, the term of this patent is extended or adjusted under 35 U.S.C. 154(b) by 1657 days.

(21) Appl. No.: 11/454,773

(22) Filed: Jun. 16, 2006

(65) Prior Publication Data
US 2006/0285640 A1 Dec. 21, 2006

Related U.S. Application Data

(60) Provisional application No. 60/691,074, filed on Jun. 16, 2005.

(51) Int. Cl.
*A61N 5/10* (2006.01)
(52) U.S. Cl. .................... 365/65; 250/492.1
(58) Field of Classification Search ............ 378/65; 250/492.1, 492.3
See application file for complete search history.

(56) References Cited

U.S. PATENT DOCUMENTS

| | | | |
|---|---|---|---|
| 6,148,272 A | 11/2000 | Bergstrom et al. | |
| 6,260,005 B1 | 7/2001 | Yang et al. | |
| 6,285,969 B1 | 9/2001 | Svatos | |
| 6,301,329 B1 | 10/2001 | Surridge | |
| 6,366,873 B1 | 4/2002 | Beardmore et al. | |
| 6,381,586 B1 | 4/2002 | Glasserman et al. | |
| 6,518,579 B1 | 2/2003 | Xu et al. | |
| 6,714,620 B2 | 3/2004 | Caflisch et al. | |
| 6,772,136 B2 | 8/2004 | Kant et al. | |
| 6,795,801 B1 | 9/2004 | Watkins et al. | |
| 2002/0027971 A1 | 3/2002 | Deasy et al. | |
| 2003/0204126 A1 | 10/2003 | Rivard | |

(Continued)

FOREIGN PATENT DOCUMENTS

WO 00/07668 2/2000

(Continued)

OTHER PUBLICATIONS

Lawrence Livermore National Laboratory article titled 3D Monte Carlo Method, dated Oct. 5, 2000, found at www.11nl.gov/peregrin/montecarlo.html.

(Continued)

*Primary Examiner* — Glen Kao
(74) *Attorney, Agent, or Firm* — Jason Freeman; O'Neal R. Mistry; Best Medical Int'l

(57) ABSTRACT

A system to provide enhanced computational efficiency in a simulation of particle transport through a medium, program product, and related methods are provided. The system can include a simulation data administrator server having access to an interaction database including records related to parameters describing interactions of particles in an absorbing medium to provide particle interaction parameters, and a simulated dose calculation computer in communication with the simulation data administrator server through a communications network. The system can also included simulated dose calculation program product stored in memory of the simulated dose calculation computer and including instructions that when executed by a processor causes the processor to perform for each of a plurality of particles deliverable from a particle source the operations of providing parameters for a medium to perform a Monte Carlo simulation to develop a map of simulated absorbed dose in the medium, and artificially adjusting simulation particle fluxes to achieve a substantially constant variance throughout a depth of the medium.

54 Claims, 11 Drawing Sheets

U.S. PATENT DOCUMENTS

| | | |
|---|---|---|
| 2004/0009455 A1 | 1/2004 | Chiang et al. |
| 2004/0202360 A1 | 10/2004 | Besson |
| 2004/0210132 A1 | 10/2004 | Manjeshwar |

FOREIGN PATENT DOCUMENTS

| | | |
|---|---|---|
| WO | 00/53262 A1 | 9/2000 |

OTHER PUBLICATIONS

Lawrence Livermore National Laboratory article titled What is Peregrine?, dated Oct. 3, 2000, found at www.11nl.gov/peregrin/what.html.

Lawrence Livermore National Laboratory article titled What Does It Do?, dated Oct. 3, 2000, found at www.11n1.gov/peregrin/whatdoes.html.

Lawrence Livermore National Laboratory article titled Why It Matters, dated Oct. 3, 2000, found at www.11n1.gov/peregrin/why.html.

Lawrence Livermore National Laboratory article titled How Does It Do It?, dated Oct. 3, 2000, found at www.11n1.gov/peregrin/how.html.

Lawrence Livermore National Laboratory article titled Peregrine Dose Calculation Engine Design, dated Oct. 3, 2000, found at www.11n1.gov/peregrin/engine.html.

Mohan, Peregrine: Improving Radiation Treatment for Cancer, article found at www.11n1.gov/str/Moses.html, printed on Apr. 13, 2006.

Wang, eta 1., Monte Carlo simulation of an optical coherence tomography signal in homogeneous turbid media; Phys. Med. Biol. 44 (1999), pp. 2307-2320.

Deasy, et al., Accelerating Monte Carlo simulations of radiation therapy dose distributions using wavelet threshold de-noising, Med. Phys. 29 (10), Oct. 2002, pp. 2366-2373.

Poster and blowup of the 15 individual sections of the poster presented at the Annual 2003 American Association of Physicists in Medicine (AAPM) meeting, Aug. 10-14, 2003, San Diego, CA.

D Lovelock, et al., A Monte Carlo Model of Photon Beams Used in Radiation Therapy, Medical Physics, vol. 22 (9), Sep. 1995, XP-002407114.

R Aaronson et al, A Monte Carlo based phase space model for quality assurance of intensity modulated radiotherapy incorporating leaf specific characteristics, Medical Physics, vol. 29 No. 12, pp. 2952-2958 (Dec. 2002).

L. Cox et al., Photon beam description in Peregrine for Monte Carlo dose calculations, proceedings of the 12th International Conference on the Use of Computers in Radiation Therapy, presented May 27, 1097, found at www.osti.gov/bridge/purl.cover.isp.

VARIANCE REDUCTION SIMULATION SYSTEM, PROGRAM PRODUCT, AND RELATED METHODS

RELATED APPLICATIONS

This Application claims priority to and the benefit of U.S. Patent Application No. 60/691,074, filed on Jun. 16, 2005, incorporated herein by reference in its entirety.

BACKGROUND OF THE INVENTION

1. Field of the Invention

The present invention relates generally to simulation of radiation transport. Particularly, the present invention relates to an improvement in radiation transport simulation. More specifically, the present invention relates to a radiation transport simulation system, program product, and related methods resulting in variance reduction.

2. Description of the Related Art

Regardless of which technique is used at the time of the diagnostic study to develop the radiation therapy treatment plan, in the delivery of either conformal radiation therapy treatments or static radiation therapy treatments, an accurate determination of radiation dose to the delivered is very important. Successful radiation therapy depends on accurately placing the proper amount of radiation upon the target without unnecessarily damaging surrounding tissue. Thus, it is necessary to relate the radiation dose determined to be delivered to the target at the time of the diagnostic study to how the radiation dose actually delivered at the time of the radiation therapy treatment. If the actual dose is not correct, the radiation dose may not be delivered to the correct location within the patient's body, possibly under-treating the target tumor or lesion and damaging healthy surrounding tissue and organs.

The Monte Carlo dose calculation method is generally considered the most accurate method to determine radiation or particle transport in heterogeneous media. Monte Carlo method has had many areas of application. For example, simulations of the physical processes of transporting neutrons and gamma rays through thick (meters) walls made of concrete and metals have been used in nuclear reactor designs, radiation protection and other purposes. The major obstacle of using Monte Carlo simulations is the slow computation speed resulting from the need to simulate tens of millions of particles at the region of interests. Depending upon various conditions, billions or even trillions of particles, depending upon the application, may need to be simulated from the radiation source. The majority of the simulation time is spent on the physical processes in the media between the radiation delivery apparatus and the region of interest. Most of the particles are absorbed and never reach the region of interest.

The efficiency of Monte Carlo code, $\epsilon$, can be defined as:

$$\epsilon = 1/(s^2 \tau)$$

where $s^2$ is the variance and $\tau$ is the computing time. In the Monte Carlo simulation of radiation transport, each particle is called a history. If N particles are generated to represent the incident photon fluence, N histories in the medium will be followed. The values of $s^2$ and $\tau$ are proportional to $N^{-1}$ and N, respectively. For a given Monte Carlo code, $\epsilon$ is a constant and its numerical value depends on the software algorithm and the computer hardware.

With respect to radiation therapy, primary photon interactions in tissue, or phantoms as tissue-equivalent medium, effectively remove primary photons from the incident radiation beam, resulting in exponential attenuation of the primary photon fluence with the penetration depth z:

$$\Phi(z) = \Phi_0 \times \exp(-\mu z)$$

where $\Phi_0$ is the primary photon fluence at the phantom surface (z=0), $\Phi(z)$ is the sane at the depth of penetration z>0 and $\mu$ is the linear attenuation coefficient for primary radiation in the medium of interest.

With respect to neutron transport, the mechanisms of interaction are essentially different from photons. They can be classified into elastic interactions and inelastic interactions. During elastic interactions, neutrons elastically deliver energy to the nuclei (especially to protons) that make the medium. During inelastic interactions neutrons transfer energy to the nuclei, leaving them in excited states, which lead to the emission of photons. There are inelastic interactions such as nuclear reactions when neutrons are absorbed, which end up with the emission of photons, protons, etc. Finally, a non-interacting neutron decays into a proton and an electron (and an anti-neutrino) with a half-life of about 15 minutes. All the above mentioned interactions can lead to an exponential decay of the primary neutron fluence.

$$\Phi(z) = \Phi_0 \times \exp(-\mu z)$$

where $\Phi_0$ is the primary neutron fluence at the phantom surface (z=0), $\Phi(z)$ is the same at the depth of penetration z>0 and $\mu$ is the linear attenuation coefficient for primary radiation in the medium of interest.

For the Monte Carlo simulation process this means that the number of available particle histories N reduces with phantom depth z as:

$$N(z) = N_0 \times \exp(-\mu z)$$

Because $s^2 \propto N^{-1}$, it can be seen that the variance of the simulated quantity, e.g. absorbed dose, increases as z increases:

$$s^2(z) = s^2(0) \times \exp(\mu z) = k \times N_0^{-1} \times \exp(\mu z),$$

where k is a proportionality coefficient and $N_0$ is the initial number of particle histories representing $\Phi_0$. To resolve this problem of deteriorating accuracy at large phantom depths z, i.e., to maintain the accuracy criterion, one can initially generate a larger number of particle histories $N_0$, which inevitably results in longer computing time.

This is where variance reduction techniques become useful. Variance reduction techniques have been either mathematical approximations or "tricks" designed to reduce the computing time $\tau$ without increasing the variance $s^2$ to thereby increase the efficiency of the Monte Carlo code. To evaluate a certain variance reduction technique, one can simply simulate the same case using Monte Carlo code without variance reduction and then with variance reduction implemented. When doing so, one requires (selects) a specific variance in the region of interest for both simulations. The efficiency gain of the variance reduction (VR) can then be defined as:

Efficiency gain=CPU time (VR off)/CPU time (VR on).

The principle behind most of these techniques is that higher priority is given to fewer number of selected histories. These histories are the most important ones contributing to the dose in the region of interest. One strategy can include avoiding spending time to propagate particles contributing little to dose, or alternatively paying more attention to "useful" particles. This includes techniques such as, for example, Russian roulette and particle splitting, energy and range rejection, Kerma approximation, interaction forcing, and biasing toward under-sampled quantities such as certain scattering angles. Another strategy can include using analytical approximations whenever possible, especially during pre- and post-simulation processing. This includes techniques such as, for example, first collision, ray tracing, correlated sampling, and wavelet de-noising. A further strategy can include a particle re-using method. Such method calculates only a few samples using Monte Carlo, and then scales the results to different location or angles. Regardless of the strategies employed, it is recognized that the Monte Carlo results should be statistically unbiased. That is, the employed strategy should not distort the expected results.

Techniques that have been applied to photon transport in Monte Carlo simulations include, for example, interaction forcing, particle splitting, and Russian roulette. In interaction forcing, many photons pass through the medium without interacting with it. Time is spent tracking these photons even though they do not contribute to the dose. These photons can be forced to interact within the simulation geometry and contribute to the statistics. In particle splitting, when a photon approaches the region of interest, it is split into $n_s$ identical sub-photons, each carrying a weight factor $1/n_s$. The calculated dose is thus unbiased and less time is wasted on photons traveling outside the region of interest. In Russian roulette, when a photon moves away from the region of interest, it is "killed" with a certain probability, K<1, and, if it "survives", its weight is increased by a factor $1/(1-K)$. Both particle splitting and Russian roulette leave the Monte Carlo simulation unbiased while computing time is spent more efficiently.

In a first collisions method, the time-consuming simulations of the primary photon interactions can be replaced with the analytically calculated collision density. This technique depends on the accuracy of pre-calculated attenuation rate of primary photons tissue. This technique is closely related to "ray tracing."

U.S. Pat. No. 6,714,620, by Caflisch et al. titled "Radiation Therapy Treatment Method" describes variance reduction through particle splitting and range rejection. U.S. Pat. No. 6,301,329, by Surridge titled "Treatment Planning Method and Apparatus for Radiation Therapy" describes variance reduction techniques including a kernel approach characterized by a filter to reduce statistical noise, and methods of splitting particles in regions of interests while discarding most of them when exiting regions of interests. U.S. Pat. No. 6,772,136, Kant et al. titled "System and Method for Financial Instrument Modeling and Using Monte Carlo Simulation" describes variance reduction techniques through importance sampling used in financial modeling. U.S. Pat. No. 6,381,586, by Glasserman et al. titled "Pricing of Options Using Importance Sampling and Stratification/Quasi-Monte Carlo" also describes variance reduction techniques including importance sampling and stratified sampling. U.S. Pat. No. 6,518,579, by Xu et al. titled "Non-Destructive in-Situ Method and Apparatus for Determining Radionuclide Depth in Media" describes a variance reduction technique that biases photon emitting angles to maximize the usage of simulated photons. U.S. Patent Application No. 20030204126 by Rivard titled "Dosimetry for Californium-252 (252Cf) Neutron-Emitting Brachytherapy Sources and Encapsulation, Storage, and Clinical Delivery Thereof" also describes a method to bias particle emissions toward the region of interest.

U.S. Pat. No. 6,366,873, by Beardmore et al. titled "Dopant Profile Modeling by Rare Event Enhanced Domain-Following Molecular Dynamics" describes a method to enhance rare events when simulating ion implantations. In this variance reduction technique, an ion is split into two and their respective weights are decreased by half, hence the overall weight factors decrease with depth while the total number of ions remain constant with depth. U.S. Pat. No. 6,148,272, by Bergstrom et al. titled "System and Method for Radiation Dose Calculation within Sub-Volumes of a Monte Carlo Based Particle Transport Grid" describes a variance reduction technique that selectively tracks those particles most likely to pass through the region of interest.

A combination of variance reduction techniques may result in noticeable improvements in Monte Carlo efficiency. It has been reported that the combination of interaction forcing, particle splitting and Russian roulette increases the efficiency of Monte Carlo simulation by a factor of 3-4. The first collision technique is reported to yield a 2-fold improvement. There is no general "recipe," however, as to which combination will perform the best.

Thus, recognized by the Applicants is the need for a new variance reduction system, program product, and related methods applicable to both homogeneous and heterogeneous absorbing media that require a significantly smaller number of initial photon histories to result in the same or better accuracy at the same selected depth of interest, that can maintain a primary particle (e.g., photon) fluence invariant with depth in the absorbing medium, and that can compensate for the artificial constancy of the particle fluence to yield unbiased results for simulated absorbed dose. Also recognized by the Applicants is the need for a new variance reduction technique which can be combined with other techniques to further improve simulation efficiency and/or accuracy.

SUMMARY OF THE INVENTION

In view of the foregoing, embodiments of the present invention provide a solution which is both cost efficient and time efficient and which includes a system, program product, and method for simulating radiation dose that incorporates new variance reduction (NVR) techniques or methodology which advantageously can increase the computing efficiency of the simulation while achieving a constant or improved accuracy and/or uncertainty (variance) in both homogeneous and heterogeneous medium.

According to embodiments of the present invention, an incident photon or other particle passing through a medium may interact or collide and thus be scattered. To compensate for such collision event, embodiments of the present invention provide artificial restoration of incident photon or other particle fluence with depth of propagation in a medium. That is, with respect to photons tracked in a simulation, a scattered photon can be "restored", i.e., re-introduced back into the incident photon fluence. If the restored photon interacts again, it is re-introduced or re-introduced back in the field again, and so on. A unique property of this technique or procedure when implemented with respect to a homogeneous medium is that the number of particle histories and the statistical uncertainty or variance of calculated absorbed dose can be made independent of depth, i.e., it can be set to be substantially constant throughout the entire simulation geometry. A weight factor applied to offspring particles resulting from the interaction (including the restored particle) can allow the simulation to remain unbiased. That is, the restoration process advantageously does not substantially distort the expected results. In a case of a divergent beam, a constant accuracy can be maintained, for example, by adjusting the particle flux according to the distance from the radiation source.

According to embodiments of a system to increase efficiency in a simulation of particle transport through a medium, when the above-described NVR technique is implemented with respect to a heterogeneous medium, even though fluence is maintained invariant, uncertainty tends to increase in low-density material due to fewer scattering events resulting from a larger particle mean free path. Correspondingly, embodiments of the system include a constant noise variance reduction (CNVR) technique or methodology which can provide a constant accuracy throughout the medium which compensates for both the flux attenuation due to absorption and the heterogeneity of the medium. In a case of a heterogeneous medium, constant accuracy can be maintained, for example, by restoring, splitting, or removing particles according to a density ratio. This density ratio is modified by a factor dependent upon the ratio of the atomic numbers between adjacent medium types if the ratio of atomic numbers between adjacent medium types is different from unity, or inversely proportional particle mean free path ratio between adjacent medium types having different compositions, which is a function of medium density and composition. According to embodiments of the system, as a result of a collision event or crossing an interface or boundary, the number of particles being tracked through the simulation can be increased or decreased depending upon the density or associated mean free path of certain portions of the medium or change in density or associated mean free path to thereby compensate for such changes.

More specifically, an embodiment of a system, for example, the system can include an image gathering device, e.g., CT scanner, accessible to a communication network to provide an at least two-dimensional image slice of a tumor target volume and an adjacent structure volume in a patient, a radiation beam source to deliver radiation to the tumor target according to a radiation treatment plan, and a radiation treatment planning computer in communication with the image gathering device and having memory, a processor coupled to the memory, and radiation treatment planning program product stored in the memory adapted to produce an optimized radiation treatment plan for delivering radiation to the tumor target volume. The system can also include a simulation data administrator server in communication with the communication network and having access to an interaction database including records related to parameters describing interactions of photons and/or other particles in an absorbing medium to provide interaction parameters. The system can further include a simulated dose calculation computer in communication with the radiation treatment planning computer and the simulation data administrator server through the communications network which includes memory and a plurality of processors coupled to the memory to calculate a simulated absorbed dose in the absorbing medium deliverable according to the radiation treatment plan. Note, the simulated dose calculation computer can function as a stand-alone computer or as a networked device, as described above.

The system can include simulated dose calculation program product stored, for example, in the memory of the simulated dose calculation computer. The simulated dose calculation program product can include instructions that, when executed by at least one of the plurality of processors, can perform the operation of modeling the tumor target volume and adjacent structure volume to define the absorbing medium. The simulated dose calculation program product can also include instructions to perform simulation operations for each of a plurality of particles, e.g., photons, deliverable from the beam source, including the operations of labeling the respective particle as a primary particle responsive to initiating a radiation delivery simulation through the absorbing medium according to a radiation treatment plan, transporting the primary particle through the absorbing medium, tracking the primary particle through the absorbing medium until undergoing a collision event, e.g., scattering event, and deeming the scattering event to have occurred. The instructions can also include those to perform the operations of consulting the interaction database responsive to the scattering event and retrieving data on the primary particle and any secondary particles resulting from the scattering event when so existing, recording energy deposited from the scattering event to thereby build a map of simulated absorbed dose, and creating a new virtual particle defining a restored virtual particle responsive to the scattering event.

Advantageously, creating the restored virtual particle to replace the original scattered particle allows the system to artificially restore incident particle fluence with depth of propagation in the absorbing medium changed in response to the scattering or other collision event. Such restoration process can also provide a substantially more constant variance (uncertainty). The original primary particle is labeled as a scattered particle and the restored virtual particle is labeled as a primary particle to be a transported, tracked, and possibly again scattered until exiting the absorbing medium. The restored virtual particle, labeled as a primary particle, inherits the properties of the primary particle except it is assigned a new weight factor. According to an embodiment of the system, any scattered virtual particles resulting from the collision or scattering event including the original primary particle is also assigned the weight factor. The weight factor functions to compensate for the effects of the artificial constancy of the particle fluence to thereby yield unbiased results for the simulated absorbed dose. Accordingly, the instructions also include those to perform the operation of producing a three-dimensional map of simulated absorbed dose delivered to the absorbing medium that is unbiased and that, in a homogeneous medium, is characterized by having a substantially constant variance (uncertainty).

Embodiments of the present invention also include methods of increasing efficiency in a simulation of particle transport through a medium. For example, a method can include the steps of selecting an original particle, e.g., photon or neutron, from a radiation source and tracking it through a medium until undergoing a collision event (e.g., absorption or scattering), consulting an interaction database responsive to the collision event and retrieving data on the original particle and each secondary particle resulting from the collision event, recording energy deposited from the collision event to thereby build a map of absorbed dose, and creating a new "virtual" particle defining a restored virtual particle responsive to the collision event to thereby artificially restore incident particle fluence with depth of propagation in the medium changed in response to the collision event. Advantageously, the restoration process can provide for maintaining primary particle fluence invariant with the depth of the medium and maintaining statistical uncertainty of simulated absorbed dose independent of depth within the medium.

Note that variations in restoration ratio can be incorporated in the process to account for differences between homogeneous and heterogeneous media. That is, when performing a simulation on a heterogeneous medium, the average number of new virtual particles created as a result of collision events throughout the medium can be adjusted for each collision event according to a ratio proportional to variations between, for example, density or particle mean free path of adjacent medium types. Alternatively, the number of particles being tracked can instead be adjusted upon transition of a boundary or interface between adjacent regions of the heterogeneous medium to account for differences in density and/or the associated particle mean free path length between the adjacent regions.

According to an embodiment of the method, the steps can also include labeling the restored virtual particle as a primary particle and the original primary particle deemed to have scattered as a scattered particle responsive to the collision event, and inheriting by the restored virtual particle all properties of the original particle except for an assigned new weight factor which can function to provide unbiased simulated absorbed dose results. The method can also include the step of producing a three-dimensional map of simulated radiation dose delivered to the medium.

Embodiments of the present invention also include methods to increase efficiency of simulations, e.g., Monte Carlo simulations, of particle transport or radiation fluxes. For example, such a method can include the steps of providing parameters for a medium to perform a Monte Carlo simulation thereon, and artificially adjusting simulation particle fluxes to achieve a substantially constant accuracy throughout a depth of the medium. According to an embodiment of the method, the step of artificially adjusting the simulation particle flux can be achieved by restoring a particle when the particle is deemed or otherwise determined to be absorbed or scattered, and assigning the restored particle a weight factor according to an attenuation coefficient and particle mean free path of the restored particle, to thereby achieve unbiased simulation final results. According to another embodiment of the method, the step of artificially adjusting the simulation particle flux can be achieved by restoring a number of particles defining restored particles when an original particle transported through the medium is deemed to be absorbed or scattered defining a collision event, scaling the number of restored particles according to a mean free path of the original particle associated with the medium at a location of the collision event, and assigning each restored particles a weight factor to thereby achieve unbiased simulation final results.

Embodiments of the present invention also include a computer readable medium to reduce computing time to increase efficiency of simulations, e.g., Monte Carlo simulations, of beam of particles that are being attenuated by arbitrary media. For example, according to an embodiment of a computer readable medium, the computer readable medium includes instructions that when executed by one or more processors cause the processor or processes to perform the operations of deeming a collision scattering event to have occurred, creating a new virtual particle defining a restored virtual particle responsive to the collision event, and labeling the restored virtual particle as a primary particle and an original primary particle deemed to have collided as a scattered particle responsive to the collision event. The operation of creating a new virtual particle defining a restored virtual particle can include restoring incident particle fluence with depth of propagation in an absorbing medium changed in response to the collision event. The instructions can also include those to perform the operation of assigning a weight factor to each scattered virtual particle to compensate for artificial constancy of the particle fluence to thereby yield unbiased results for calculating simulated absorbed dose, and assigning a weight factor to each restored virtual particle resulting from the collision event to compensate for the artificial constancy of the particle fluence to thereby yield unbiased results for calculating the simulated absorbed dose.

According to an embodiment of the present invention, a computer readable medium can include instructions that when executed by one or more processors cause the processor or processors to perform the operations of providing parameters for a medium to perform a Monte Carlo simulation thereon, and artificially adjusting simulation particle fluxes to achieve a substantially constant variance throughout a depth of the medium. According to an embodiment of the computer readable medium, the operation of artificially adjusting the simulation particle flux can be achieved by restoring a particle when the particle is deemed to be absorbed or scattered and assigning the restored particle a weight factor according to an attenuation coefficient and particle mean free path of the restored particle to thereby achieve unbiased simulation final results. According to another embodiment of the computer readable medium, the operation of artificially adjusting the simulation particle flux can be achieved by restoring a number of particles defining restored particles when an original particle transported through the medium is deemed to be absorbed or scattered defining a collision event, scaling the number of restored particles according to a mean free path of the original particle associated with the medium at a location of the collision event, and assigning each restored particles a weight factor to thereby achieve unbiased simulation final results.

According to embodiments of the present invention, a new variance reduction technique is provided which is based on the artificial restoration of incident particle fluence, e.g., particle fluence, with depth of propagation in a medium. Without compromising the accuracy of the Monte Carlo data, the new technique can increase Monte Carlo efficiency significantly, maintain primary particle fluence invariant with depth, and/or through use of weight factors, provide unbiased results for simulated absorbed dose. A unique property of the new technique is that the statistical uncertainty (noise) of Monte Carlo calculated absorbed dose in a medium can be made independent of depth, i.e., constant throughout the entire simulation geometry. Advantageously, the systems, program product, and methods according to embodiments of the present invention can improve the efficiency of Monte Carlo simulations by a factor in the range of 5-100 or more, depending on the area of applications. To do so, embodiments of the present invention can utilize a significantly smaller number of initial histories over that of conventional systems yet still deliver the same or improved accuracy, uncertainty, or variance at a certain depth of interest. The increase of Monte Carlo efficiency can be appreciated in the cost effectiveness. For example, when conducting a radiation treatment planning procedure, ~10 fields may need to be calculated. To finish such a task in less than, e.g., an hour using Monte Carlo software or code without the NVR techniques, a cluster of ~100 computers or so may be necessary. With the improvement of a factor of 10 in the software or program product algorithm, a cluster of only, e.g., ~10 computers or processors would be sufficient for the same radiation treatment plan. This requirement is generally considered affordable and in a practical range for the hardware requirements. Advantageously, the new technique can also be readily combined with other variance reduction techniques for further enhancement of Monte Carlo efficiency. Further, advantageously such systems, program product, and methods can also be incorporated in nuclear engineering and radiation safety, medical imaging, radiation therapy, and other applications involved with particles or radiation traversing various media.

BRIEF DESCRIPTION OF THE DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope as it may include other effective embodiments as well.

DETAILED DESCRIPTION

The present invention will now be described more fully hereinafter with reference to the accompanying drawings, which illustrate embodiments of the invention. The present invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout. Prime notation, if used, indicates similar elements in alternative embodiments.

Many different fields or areas are confronted with the same challenge of computation efficiency. These fields can include, for example: simulations of space radiation upon the earth's atmosphere; radiation safety for astronauts; medical X-ray imaging using KeV photons; and intensity modulated radiation therapy using, e.g., MeV photons, just to name a few. The description below, for simplicity, however, will focus on radiation therapy planning incorporating new variance reduction ("NVR") techniques or methodologies designed to dramatically increase, e.g., Monte Carlo ("Monte Carlo") simulation efficiency. As shown in FIGS. 1-17, embodiments of the present invention include systems 30, program product 71, and techniques or methods designed to reduce computing time to increase efficiency, for example, of Monte Carlo simulations of a beam of particles, e.g., photons or neutrons, etc., that are being attenuated by arbitrary media. Note, although "variance reduction" is used herein to describe embodiments of the present invention, variance reduction is nevertheless an outcome of the described intelligent systems and methods that result in reduced variance.

Figure 1A:
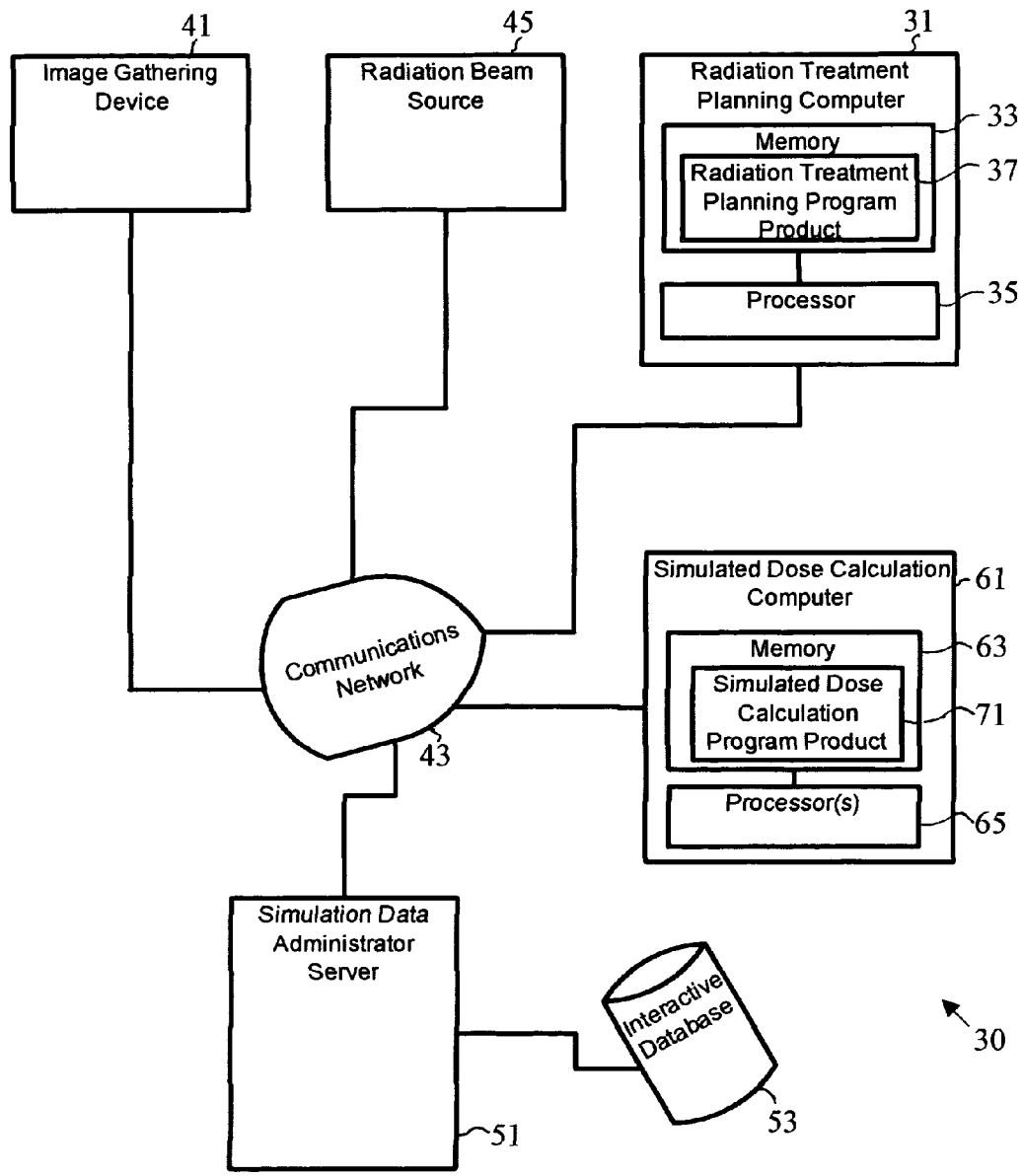
FIG. 1A is a schematic diagram of a system to increase efficiency in a simulation of particle transport through a medium according to an embodiment of the present invention.
Figure 1B:
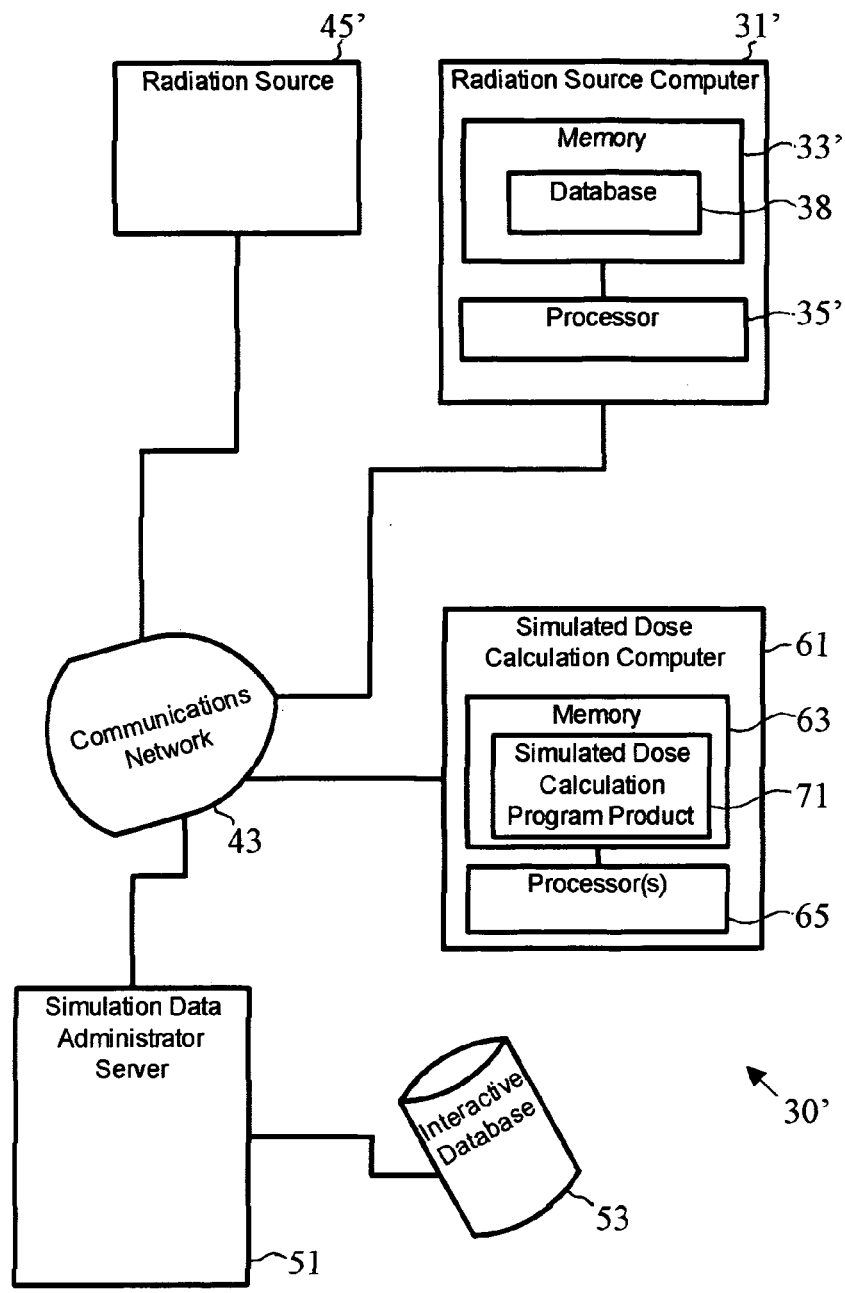
FIG. 1B is a schematic diagram of a system to increase efficiency in a simulation of particle transport through a medium according to an embodiment of the present invention.

As shown in FIG. 1A-1B, embodiments of the present invention include systems to increase efficiency in a simulation of particle transport through an absorbing medium (phantom/patient) and/or to reduce the variance in the simulation by maintaining primary particle fluence invariant with the depth of the absorbing medium. For example, a system 30 (FIG. 1A) can include a radiation treatment planning computer 31 having memory 33, a processor 35 coupled to the memory 33, and radiation treatment planning program product 37 stored in the memory 33 adapted to produce an optimized radiation treatment plan for delivering radiation to the tumor target volume, and an image gathering device 41, e.g., computed tomography (CT) scanner or other imaging device known to those skilled in the art, accessible to a communication network 43 to provide stacks of two-dimensional image slices or a three-dimensional image of a tumor target volume and an adjacent structure volume in a patient or phantom used to develop the treatment plan. The system 30 also includes a radiation beam source 45, e.g., linear accelerator or other delivery device known to those skilled in the art, to deliver radiation to the tumor target according to the radiation treatment plan. The radiation can be in the form of photons, neutrons, electrons, protons, or other particles. The system 30 can also include a simulation data administrator server 51 having access to an interaction database 53 including records related to parameters describing interactions of photons or other particles in an absorbing medium to provide a simulated dose calculation computer 61 photon and/or other particle interaction parameters.

The system 30, accordingly, includes the simulated dose calculation computer 61 which is in communication with the radiation treatment planning computer 31 and the simulation data administrator server 51 through the communications network 43. The simulated dose calculation computer 61 includes memory 63 and at least one but preferably a plurality of processors 65 coupled to the memory 63 forming a computer array to calculate a simulated absorbed dose in the absorbing medium deliverable according to the radiation treatment plan. Note, as will be described in more detail later, simulations of radiation absorbing, such as, for example, Monte Carlo simulations, are straightforward for parallel processing because the interactions among the histories are negligible, hence the histories can be added independently. Accordingly, the simulated dose calculation computer 61 can either have multiple processors 65 or can be a plurality of computer 61 each having one or more processors. Note also, the memory 63 can include volatile and nonvolatile memory known to those skilled in the art including, for example, RAM, ROM, and magnetic or optical disks, just to name a few. Note further, the radiation treatment planning computer 31, image gathering device 41, simulation data administrator server 51, and the simulated dose calculation computer 61, or combination thereof, can be embodied in a single apparatus within the same housing or in separate housings.

A simulated dose calculation program product 71 stored, for example, in the memory 63 of the simulated dose calculation computer 61, can include instructions that when executed by at least one of the plurality of processors 65 performs functions to increase efficiency in the simulation of particle transport through an absorbing medium (phantom/patient) and/or to reduce the variance in the simulation by maintaining primary particle (e.g., photon) fluence invariant with the depth of the absorbing medium. Note, the program product 71 can be in the form of microcode, programs, routines, and symbolic languages that provide a specific set or sets of ordered operations that control the functioning of the hardware and direct its operation, as known and understood by those skilled in the art. The simulated dose calculation program product 71 will be described in more detail later.

According to embodiments of the present invention, the simulated dose calculation computer 61 having simulated dose calculation program product 71, simulation data administrator server 51, and interactive database 53 are readily applicable to other areas which deal with particle transport through an absorbing medium including but not exclusively: nuclear reactor design and radiation shielding; x-ray imaging simulations involving low energy (KeV) photons hence large attenuations in tissue; simulation of particle deposition processes used to dope semiconductors in wafer fabrication; astronaut radiation safety considerations; simulations of earth atmosphere and space environment interactions; electronic transport in heterogeneous semiconductors especially involving electronic impact ionizations; and modeling of transportation system involving traffic jams, just to name a few. For example, system 30' (FIG. 1B) illustrates a nuclear reactor/shielding design implementation. The system 30' can include a radiation source computer 31' having memory 33', a processor 35' coupled to the memory 33', and a database 38 stored in the memory 33' or otherwise accessible to processors 35', 65, and containing data including an indication of distribution of the radiation source or sources 45', intensities, and attributes of the surrounding structure, e.g., whether the shielding structure is metal or concrete, the density, the thickness, etc. A simulated dose calculation program product 71 stored, for example, in the memory 63 of the simulated dose calculation computer 61, can include instructions that when executed causes the computer 61 to perform functions as described previously using data from the database 38 and data from the interactive database 53 to more efficiently model particle transport through an absorbing medium (e.g., radiation shield) and/or to reduce the variance in the simulation by maintaining primary particle fluence invariant with the depth of the absorbing medium.

Figure 2:
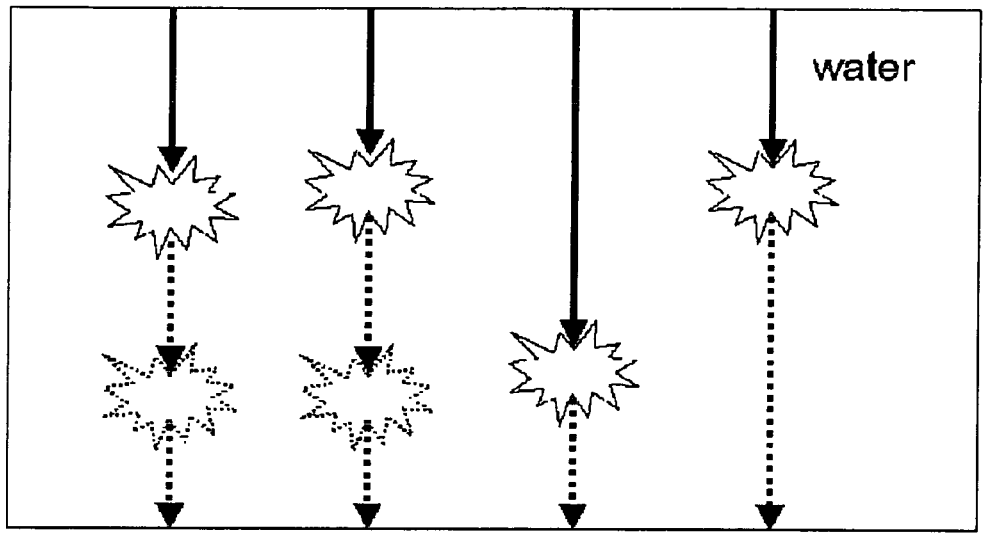
FIG. 2 is a schematic diagram illustrating virtual particle restoration according to an embodiment of the present invention.
Figure 3:
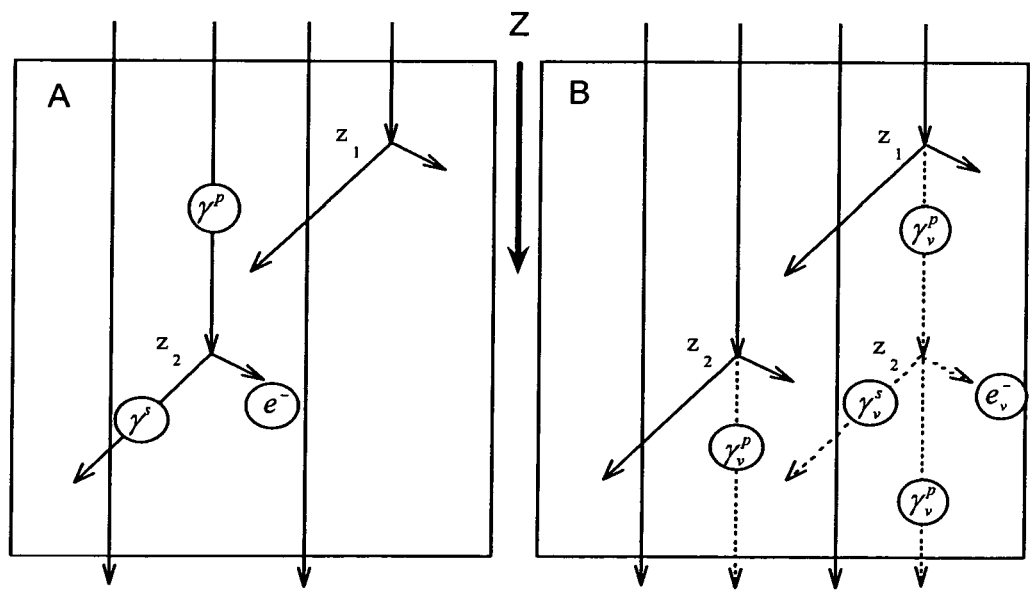
FIG. 3A is a schematic diagram illustrating fluence attenuation resulting from a collision event in a simulation not applying embodiments of the present invention.
FIG. 3B is a schematic diagram illustrating photon restoration due to a collision event in a simulation according to an embodiment of the present invention.

Embodiments of the present invention also include methods or techniques to increase efficiency in the simulation of particle transport through an absorbing medium (phantom/patient) and/or to reduce the variance in the simulation by maintaining primary particle fluence invariant with the depth of the absorbing medium. FIGS. 2-3B illustrate the radiation of a water phantom by a parallel, monoenergetic photon beam. The solid lines represent real photons $\gamma^p$ and dashed lines represent "virtual" photons $\gamma_v^\gamma$, described below. In general, an incident particle, e.g., photon for illustration, passing through the medium may interact, and thus be absorbed or scattered, resulting in an exponential attenuation in primary photon flux with the depth z. As the primary photon flux attenuates, statistical uncertainty of absorbed dose increases with z as $(N_z)^{-1/2}$, where $N_z = N_0 \cdot \exp(-\mu z)$ is the number of photons available at depth z, $N_0$ is the number of initial number of photons, and $\mu$ is the linear attenuation coefficient for primary radiation. If at a depth of interest d, e.g., 30 cm (see, e.g., FIG. 7), $N_d$ yields an acceptable dose uncertainty, then instead of $N_0$ initial histories, one can use $N_d$ histories if this number is maintained invariant with medium depth. This can be accomplished by "recovering" or "restoring" each interacted primary photon back into the incident primary photon fluence, thus making it available to interact again. If restored virtual photon interacts again, the restored photon can be again reintroduced in the field again, and so on. This procedure beneficially can result in the number of histories being constant with phantom/patient depth and also can result in variance being independent of depth.

The secondary or offspring particles, e.g., those resulting from both real and virtual interactions, can be given a dose weight factor corresponding to the depth z of the primary photon interaction to thereby maintain the simulation unbiased. In a simple case of monoenergetic, parallel photon beam in a homogeneous medium undergoing a Monte Carlo simulation, this dose weight factor should be, for example, a value proportional to $\exp(-\mu z)$. That is, the weights are adjusted as necessary so that the expected results are not distorted by the restoration process. Because $N_d \ll N_0$, computing time can be significantly reduced by adjusting $N_0$ to a value approximating that of $N_d$. That is, for a given level of accuracy for a desired depth of interest d, the number of histories $N_0$ and thus computing time can be significantly reduced. Alternatively, uncertainty can be significantly enhanced by setting $N_0$ as some value between $N_0$ and $N_d$. Note, the term "accuracy" as used herein generally refers to a representation of a ratio of expected values to actual and/or calculated values. The term "bias" as used herein generally refers to distortion of the nature of a process.

An illustration of the results of a restoration process necessitated by Compton scattering is illustrated in FIGS. 3A and 3B. As shown in FIG. 3A, primary photon, $\gamma^p$, interacts with an atomic electron yielding a scattered photon, $\gamma^s$, and a Compton electron, $e^-$. In FIG. 3A there are four incident particles (or histories) and only two exiting particles, which provide an indication of the primary fluence attenuation with medium depth. One can restore primary photon $\gamma^p$ as shown in FIG. 3B. In this scenario, the outcome of the interaction will be a scattered photon, $\gamma^s$, a Compton electron, $e^-$, and one more particle, a virtual photon, $\gamma_v^p$. This latter particle $\gamma_v^p$ is identical to the original primary photon $\gamma^p$ as it is of the same energy and it travels along the same path as $\gamma^p$. If virtual photon $\gamma_v^p$ interacts again before escaping simulation geometry, it is again restored. Note that in FIG. 3B, the number of incident and exiting particles is now the same, which is an indication of primary fluence that is constant with medium depth. When returning every interacted primary photon (real or virtual) back into the field, the system can keep the number of histories constant with depth z, that is $N(z)=N_0=$const. In this configuration, the variance $s^2$ is no longer a function of depth z. Note, such consideration is also valid for photoelectric effect and pair production.

Figure 4:
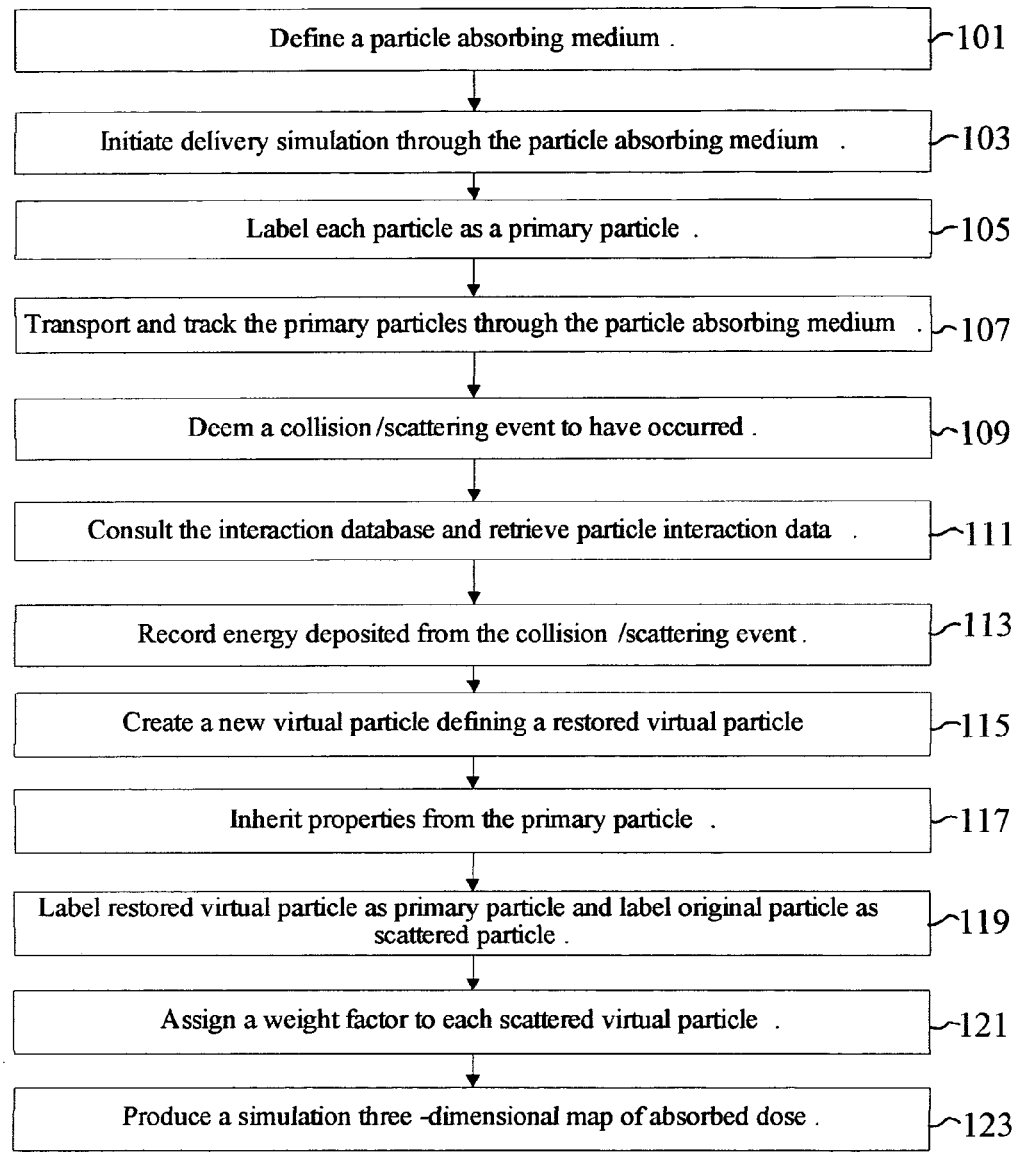
FIG. 4 is a schematic flow diagram illustrating a method of propagating photons through a medium according to an embodiment of the present invention.
Figure 5:
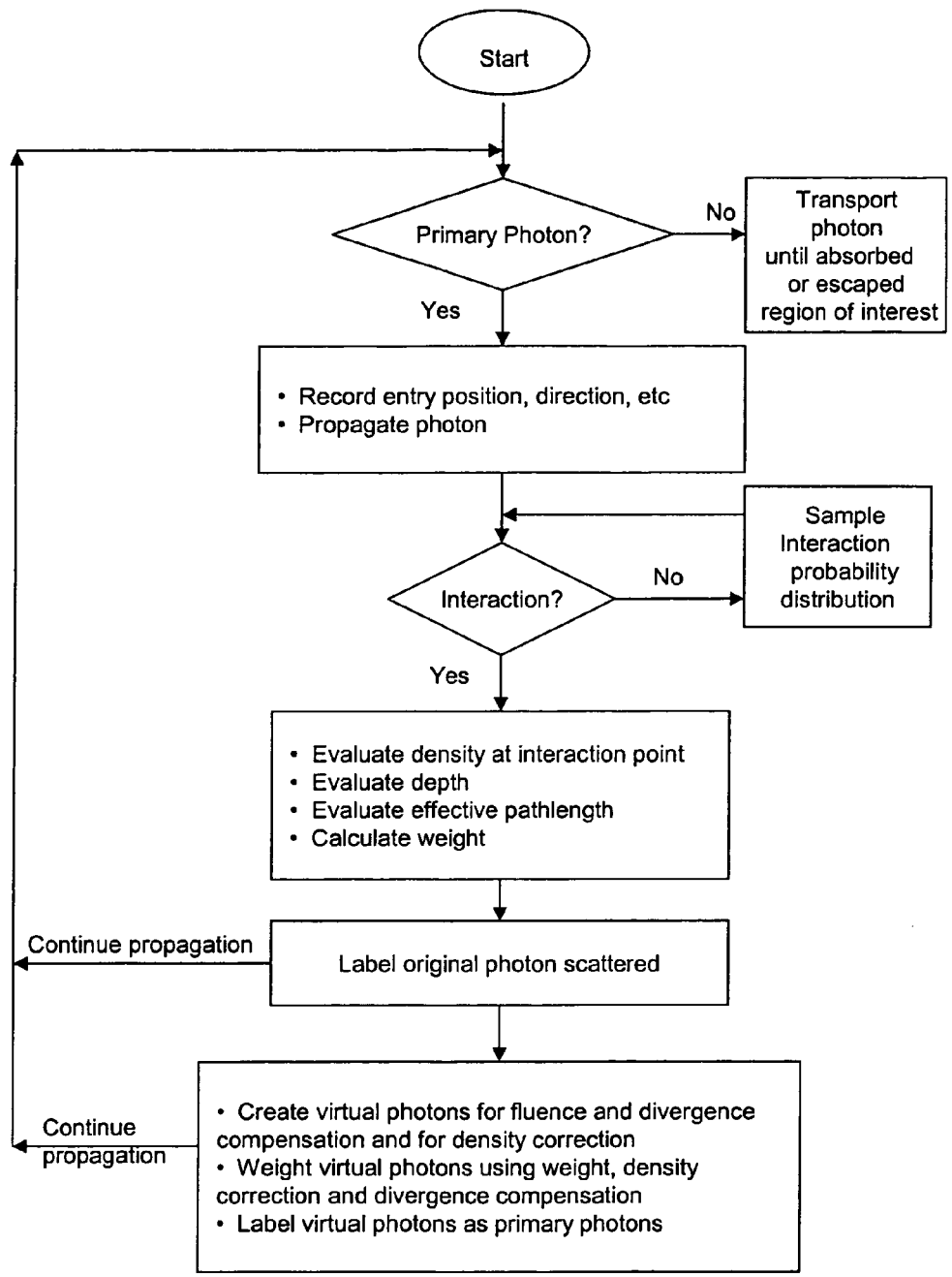
FIG. 5 is a schematic flow diagram illustrating a method of propagating photons through a medium according to an embodiment of the present invention.

As shown in FIGS. 4 and 5, the operations to be performed by the simulated dose calculation program product 71 according to an embodiment of the present invention are described below. As noted previously, conventional Monte Carlo simulations of photon transport follow realistic exponential attenuation of photon fluence in the media. In the case of a monoenergetic, parallel photon beam in, for example, a water phantom, $N_0$ initial photons (histories) will be reduced to $N_z=N_0 \cdot \exp(-\mu z)$, where $\mu$ is the linear attenuation coefficient for primary photons in water and z is a variable representing the depth in the phantom (not to be confused with d representing a specified "depth of interest"). Hence, in conventional Monte Carlo simulations the statistical uncertainty (i.e., noise) of calculated dose increases with depth z. In the Monte Carlo simulations implementing the techniques of the present invention termed "NVR on" in the figures, the primary photon fluence is made to be invariant with the depth z.

According to embodiments of the simulated dose calculation program product 71 implemented in a Monte Carlo simulation of radiation dose deliverable according to a radiation treatment plan, in order to produce the simulation, the tumor target volume and adjacent structure volume is first modeled to define the absorbing medium (block 101). Once the delivery simulation is initiated (block 103), each photon from the radiation beam source 45 is labeled as a primary photon (block 105). Each photon is transported and tracked through the medium (block 107), e.g., patient or phantom, until each photon, if at all, is deemed to encounter a collision event, e.g., Compton scattering, pair production, photo-electric effect, or coherent scattering. Such determination can be made through use of, for example, a sample interaction probability distribution. When such a collision event, e.g., scattering event is deemed to happen (block 109), the interaction database 53 can be used to describe the effect of the collision event (block 111). Referring to scattering for illustrative purposes, energy deposited from the scattering event is recorded (block 113) and a new, "virtual" photon is created (block 115). The restored virtual photon is labeled as a primary photon, while the real photon is labeled after scattering as a scattered photon (block 119). According to an embodiment of the simulated dose calculation program product 71, the scattered photons will not be restored in further scattering events.

Each restored virtual photon can inherit or otherwise be provided the properties from the respective previous primary photon (block 117), except that it is assigned a new weight factor:

$$W_h = W_{h-1} \exp(-R),$$

where $W_{h-1}$ is the weight factor of the photon before the scattering event, and R is the radiological path length between the current location and the previous location where the photon was last assigned the weight factor $W_{h-1}$. According to an embodiment of the method, radiological path length R is represented by $\Sigma \mu_i z_i$. The attenuation coefficient $\mu_i$ within each step length $z_i$ is calculated using the photon mean free path, which is a function of the photon energy and the average material density within $z_i$. A fixed step length of $z_i=0.1$ cm that is smaller than the resolution of a typical patient CT scan has been chosen for the illustration. This step size should be adjusted for different applications. Following the weight factor $W_h$ assigned to the newly restored virtual photon, the offspring particles and hence their dose contributions, can be provided the same weight factor $W_h$ (block 121). If the restored virtual photon is scattered again, it is further restored with the new weight factor $W_h$, but having parameters associated with the new temporal and spatial location. Upon completion of the transport portion of the simulation, a three-dimensional map of simulated absorbed dose delivered to the phantom or patient can be displayed to a user (block 123).

Determining $\Sigma \mu_i z_i$ is not the only methodology of evaluating radiological path-length. For example, given a primary particle propagation path (vector), a voxel-dependent array of radiological path-lengths ($d_{eff}(I)$) can be pre-calculated and stored taking advantage of the finite size of the voxel and perhaps interpolating, where I refers to a given voxel. Thus, the radiological path-length R between two points where scattering events on the primary/restored particle (photon) occur can be described as the difference between the values of the pre-calculated array evaluated at those two points, e.g., $d_{eff}(I_h) - d_{eff}(I_{h-1})$.

For a heterogeneous medium including multiple regions of different medium (material) types, some of the above described operations are modified to account for corresponding variations in statistical uncertainty, number of scattering events, and mean free path between different medium types, to thereby provide improved efficiency with constant uncertainty or variance and/or improved uncertainty or variance. For example, according to an embodiment of the simulated dose calculation program product 71, rather than restore scattered primary photons at a ratio of one-to-one, when a collision occurs in a second medium type of the heterogeneous medium, an average number of photons are instead restored according to a scaling factor approximately equaling a ratio approximately equal to a second density $\rho 2$ of a second medium type of the heterogeneous medium to a first density $\rho 1$ of a first medium type and/or a ratio of a first photon mean free path to a second photon mean free path associated with the different medium types. Correspondingly, the weight factor $W_h$ is adjusted so that the weight factor is defined as:

$$W_h = W_{h-1} \exp(-R)(x_2/x_1),$$

wherein the ratio $x_2/x_1$ is defined as either a function of the ratio of the second density $\rho 2$ to the first density $\rho 1$ or the ratio of the first particle mean free path to the second particle mean free path, depending upon the algorithm configuration. If the medium contains heterogeneities with substantially different atomic numbers (Z), then the number of photons should be altered in a manner somewhat different from the ratio of densities, since the effect of pair creation or photo-electric effect will be more significant. The dependence on Z (more important at low photon energies) is cubic, and for pair creation, will be linear in Z. Thus, the above equation should be modified by adding a correction factor dependent on the energy and the ratio of the average atomic numbers, such that if $Z_2/Z_1$ is unity, the factor will be one. This factor can be denoted $f(E, Z_2/Z_1)$, where E refers to the particle energy, and weight factor $W_h$ is adjusted so that the weight factor is defined as:

$$W_h = W_{h-1} \exp(-R)(x_2/x_1)(f(E, Z_2/Z_1)).$$

Figure 15:
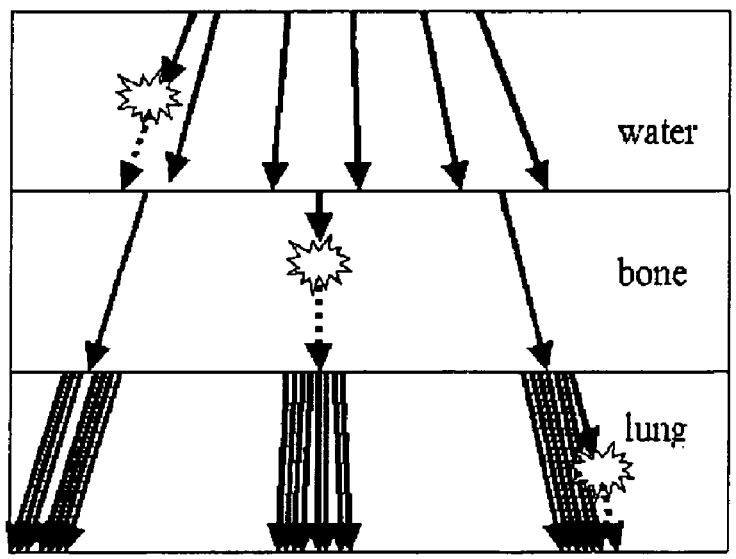
FIG. 15 is a schematic diagram illustrating virtual photon restoration in a heterogeneous medium according to an embodiment of the present invention.

Alternatively, to compensate for the variations in statistical uncertainty, number of scattering events, and/or mean free path between different medium types, as perhaps best shown in FIG. 15, the simulated dose calculation program product 71 can include instructions to perform the operations of randomly removing primary photons at a removal probability in response to photons passing an interface between a first medium type, e.g., water, and a second medium type, e.g., bone, having a higher density than the first medium type. The instructions can also include thus to perform the operation of splitting the primary photons into a number of particles, on average, in response to primary photons passing an interface between the second medium type, e.g., bone, and a third medium type, e.g., lung, having a lower density than the first medium type. In this illustration, the removal probability and the approximately proportional to the density ratio of the first medium type to the second medium type or the mean-free-path ratio of the second medium type and the first medium type, and the number of split primary photons can be approximately proportional to the density ratio of the second medium type to the third medium type or the mean-free-path ratio of the third medium type and the second medium type.

Figure 6:
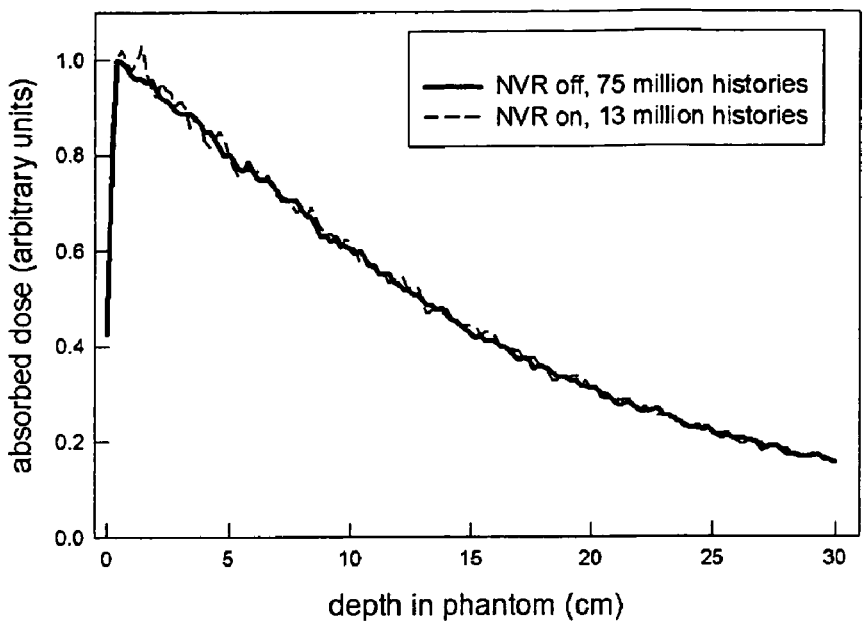
FIG. 6 is a graph of comparative depth-absorbed dose curves illustrating relative error according to an embodiment of the present invention.
Figure 7:
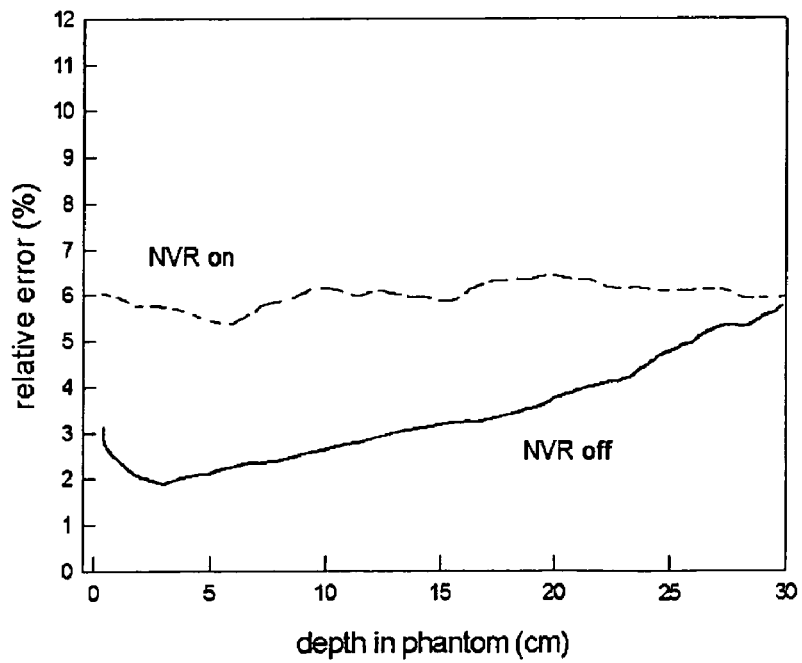
FIG. 7 is a graph of comparative depth-relative error curves illustrating relative error for the curves illustrated in FIG. 5 according to an embodiment of the present invention.

In the following text, illustrated are results of implementation on a homogeneous medium of the system 30, 30', program product 71, and methods described above, collectedly referred to as NVR. A meaningful comparison of the efficiency of Monte Carlo software, program product, or code, with NVR and without NVR, denoted as "NVR on" and "NVR off", respectively, can be accomplished by requiring, for both cases, the same accuracy of simulated dose at the depth of interest d in a phantom or patient. FIGS. 6 and 7 show the variation of central-axis absorbed dose with depth in water for a 1.25 MeV monoenergetic photon beam, with a field size of 4 cm×4 cm at the surface of the water. In the case of "NVR off," 75 million initial histories result in a 2% dose uncertainty at a depth of 1 cm. The uncertainty increases to about 6% at 30 cm. If, for example, d=30 cm is the depth of interest and we desire a 6% uncertainty in absorbed dose at this depth, then with "NVR on," the system 30 can achieve this level of accuracy using, for example, only 13 million initial histories. Note, at shallow depths, the absolute errors can be larger for the "NVR on" case than for the "NVR off" case. In the "NVR on" case, however, the relative error, i.e., noise, remains constant with depth, as shown in FIG. 7. Even though restoring and transporting virtual photons takes some computing time, in this illustration, a net efficiency gain is found to be approximately 1.8. Beneficially, this procedure is valid in the case of any number of initial histories and any specified uncertainty.

Figure 8:
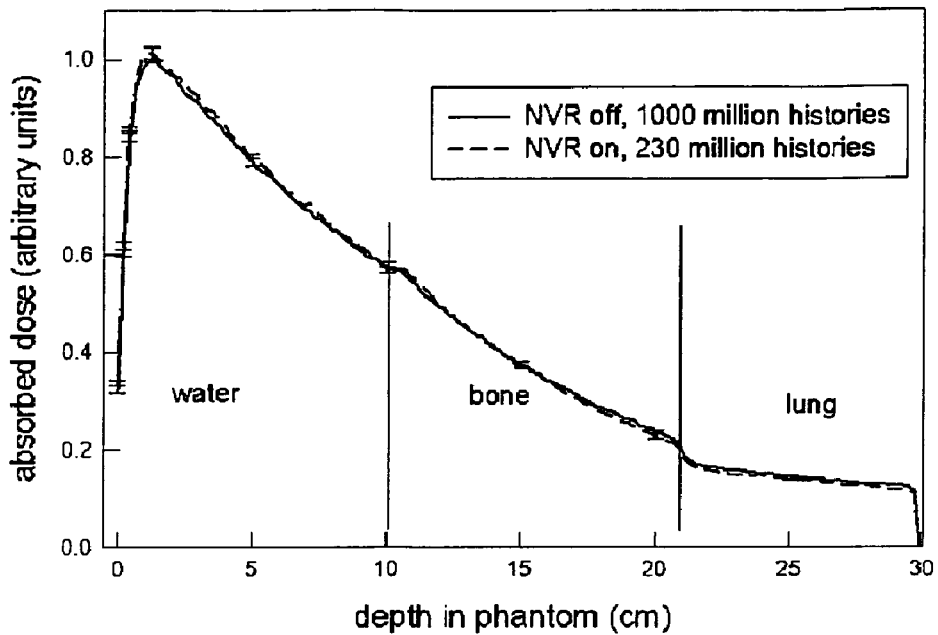
FIG. 8 is a graph of comparative depth-absorbed dose curves for a heterogeneous medium illustrating relative error according to an embodiment of the present invention.

Similarly, FIG. 8 shows that NVR is unbiased in the case of a 6 MV X-ray beam with a field size of 7 cm×7 cm in a heterogeneous phantom of layered geometry, e.g., 10 cm of water, 10 cm of bone, and 10 cm of lung. In this case, a 3% statistical uncertainty is specified at a depth of interest d=25 cm. As illustrated, NVR can beneficially maintain a constant primary photon fluence throughout the phantom with a slight modification from that used with respect to a purely heterogeneous medium. Because the photon mean free path is larger in the lung, for example, there are fewer scattering events per unit volume; hence the variance increases in the lung. The use of NVR without modification in this case nevertheless leads to an efficiency gain of approximately 1.9.

Figure 9:
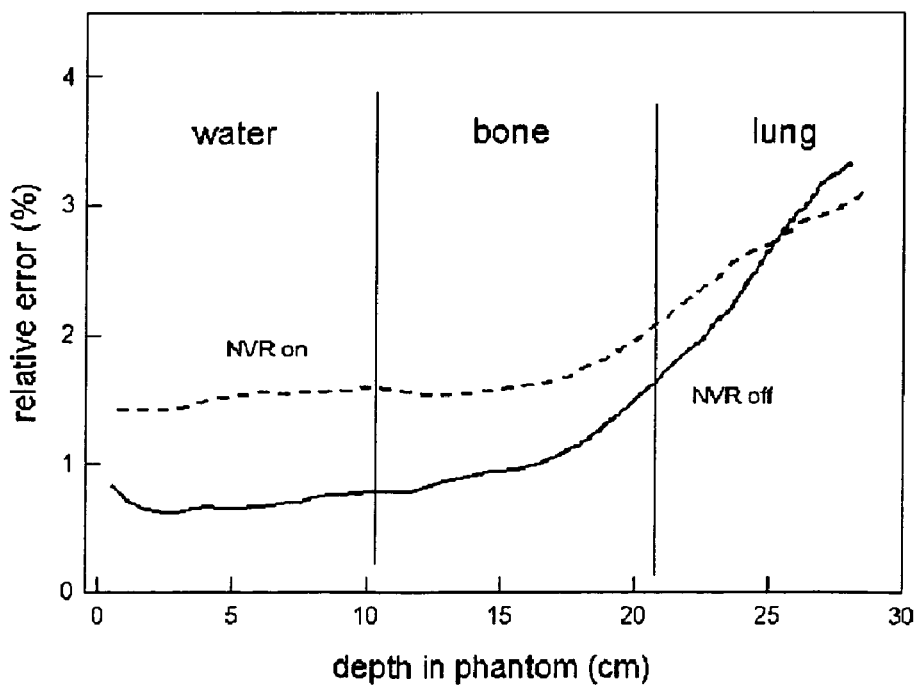
FIG. 9 is a graph of comparative depth-relative error curves illustrating relative error for the curves illustrated in FIG. 7 according to an embodiment of the present invention.
Figure 10:
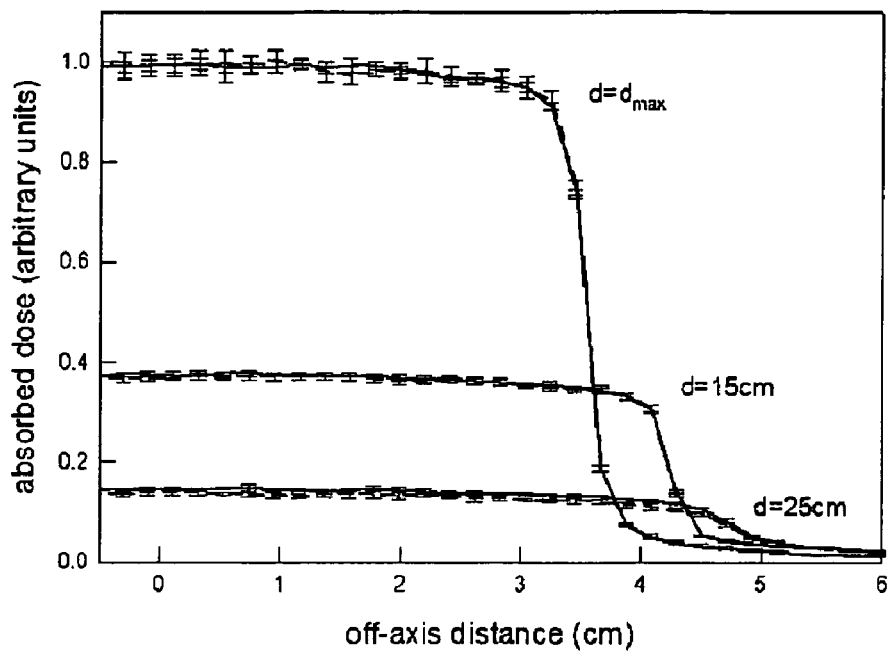
FIG. 10 is a graph of comparative dose profiles at various depths illustrating relative error at various off-axis distances according to an embodiment of the present invention.

FIG. 9 shows the relative errors corresponding to the depth-dose curves in FIG. 8. The solid line indicates the relative error for "NVR off." The dashed line indicates the relative error for "NVR on." FIG. 10 shows the dose profiles at various depths d=$d_{max}$, d=15 cm, and d=25 cm, illustrating relative error at various off-axis distances. Again it should be noted that at $d_{max}$ the error bars are larger for the "NVR on" case, due to the smaller number of initial histories used. At the depth of interest, i.e., d=25 cm, however, both cases have a 3% relative error.

Figure 11:
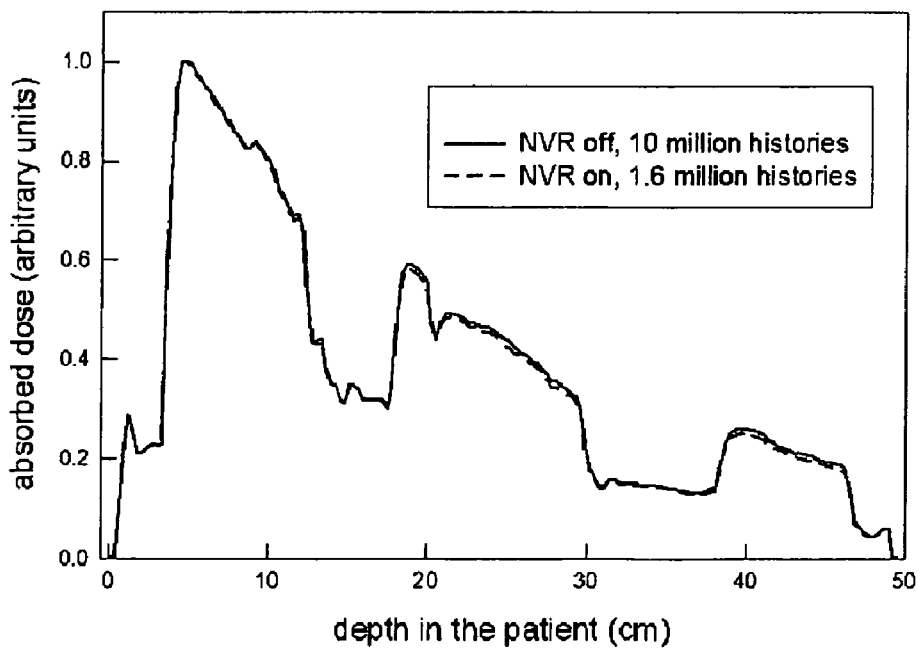
FIG. 11 is a graph of comparative depth-absorbed dose curves illustrating relative error according to an embodiment of the present invention.

FIG. 11 shows that NVR is unbiased in the case of a 6 MV X-ray beam with a field size of 0.5 cm×0.5 cm in a CT-based patient anatomy and is provided to demonstrate the effects of low-density heterogeneity (lung) that is due to the electronic disequilibrium. It can be seen that the depth-dose curve calculated using NVR scheduling follows to the smallest details of that calculated with "NVR off." An efficiency gain factor of 4.5 is achieved for a 2% accuracy specified at d=40 cm in the patient.

Figure 12:
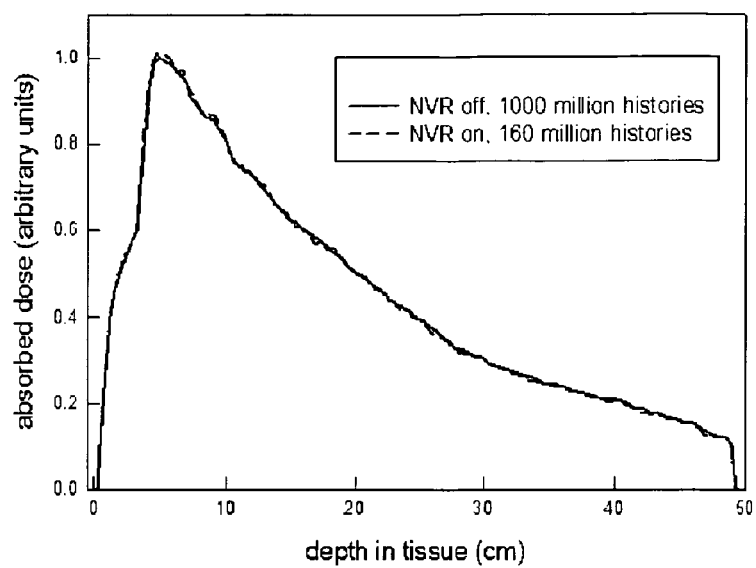
FIG. 12 is a graph of comparative depth-absorbed dose curves illustrating relative error according to an embodiment of the present invention.
Figure 13:
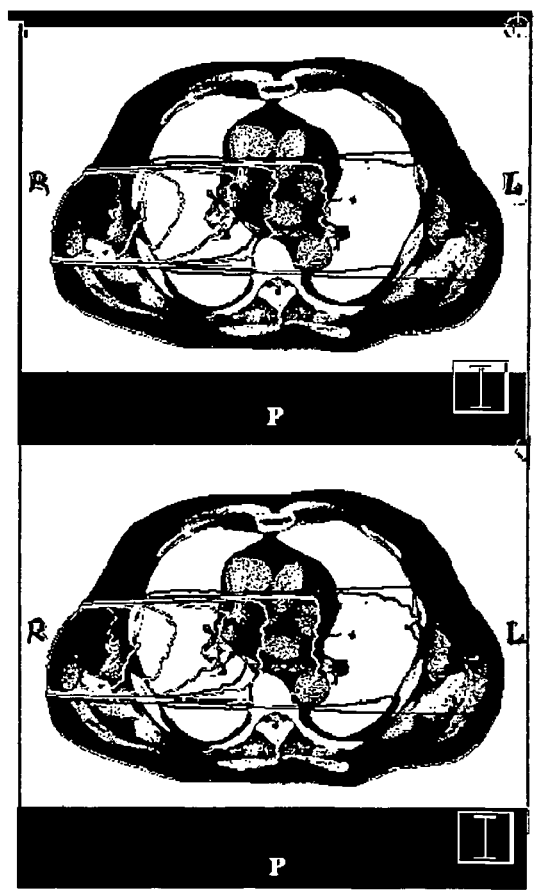
FIG. 13 is a pair of comparative graphical CT images overlaid with isodose contours illustrating unbiased results according to an embodiment of the present invention.
Figure 14:
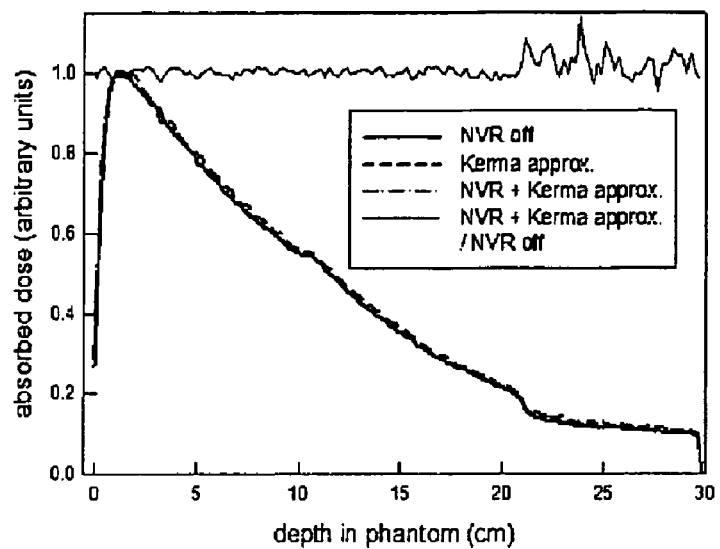
FIG. 14 is a graph of comparative depth-absorbed dose curves illustrating relative error and a curve illustrating a bias ratio according to an embodiment of the present invention.

Similarly, FIG. 12 shows the depth-dose curves for a 6 MV X-ray beam with a field size of 10 cm×10 cm field in the CT-based patient (heterogeneous) anatomy, but with substantially larger histories, 1000 million histories with "NVR off" and 160 million histories with "NVR on" resulting in uncertainty being "smoothed out" by an increased number of collision (e.g. scattering) events. FIG. 13 shows the corresponding isodose contours overlaid on the CT images with "NVR off" (top frame) and with "NVR on" (bottom frame) are practically indistinguishable. Particularly, the top frame shows dose traits using the 1000 million histories with "NVR off." The bottom frame shows substantially the same dose traits using only 160 million histories with "NVR on." Note, the individual lines shown represent 90%, 80%, 70%, 60%, 50%, 43%, 40%, 30%, 20%, and 10% of the maximum dose.

According to embodiments of the present invention, NVR is compatible with other techniques that result in reducing computation time in Monte Carlo simulations. Beneficially, the combined efficiency gain can be multiplicative of individual contributions. For example, NVR can be implemented together with a "Kerma approximation" known and understood by those skilled in the art. The idea is based on the fact that the ratio between scatter dose and scatter Kerma is very close to one. Implementing the Kerma approximation includes first identifying if an electron is an offspring of a primary photon or that of a scattered photon. If the electron is an offspring of a primary photon, the electron is tracked as with NVR alone. If the electron is an offspring of a scattered photon, the kinetic energy of the electron is deposited on the point of collision and the electron is removed from the system (simulation). Performing such steps can provide an additional efficiency gain of ~1.2. This gain factor is multiplicative to the efficiency gain from NVR. Simulation depth-dose curves for NVR off, the Kerma approximation only, and NVR implemented with Kerma are compared in FIG. 14. Also shown is a substantially horizontal plot of absorbed dose determined using NVR implemented with Kerma divided by that with "NVR off" indicating that even when implemented with the Kerma approximation, NVR remains substantially unbiased.

For the CT-based patient anatomy, an efficiency gain of ~2 can be achieved for typical field sizes. The NVR technique described above is, however, more effective for higher-density materials, such as metals, where attenuation coefficients are much larger than those for water. An efficiency gain of ~10 has been obtained when transporting 6 MV photons through a steel-water phantom made of a 10 cm layer of steel and a 20 cm layer of water. This has an important implication, i.e., when the above described NVR technique is applied to the photon transport through the blocks, wedges, MLCs or compensators, there is generally a corresponding larger gain in computation efficiency.

Figure 16:
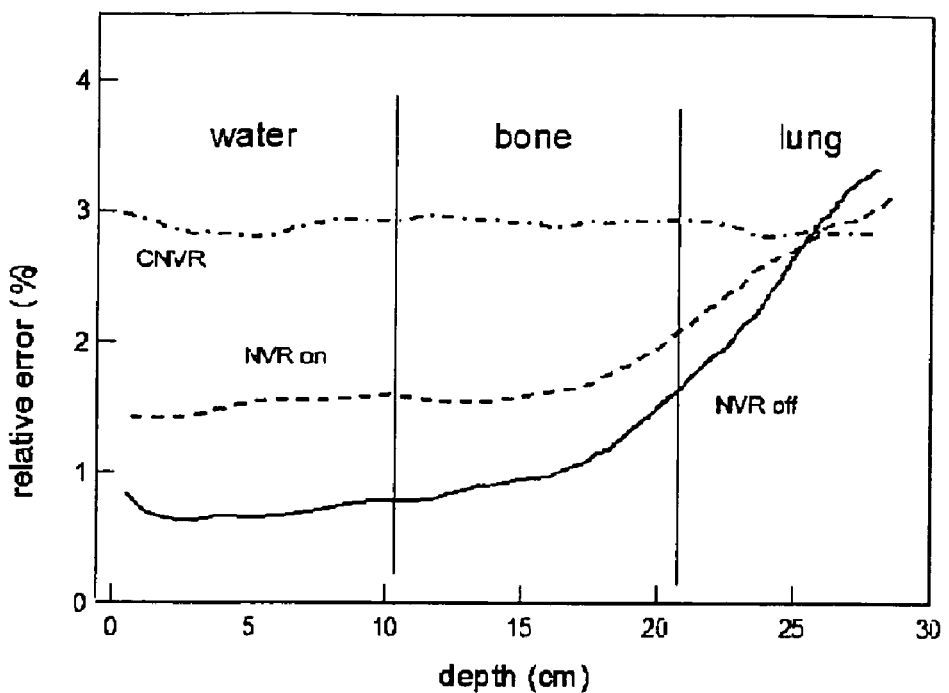
FIG. 16 is a graph of comparative depth-relative error curves illustrating relative error according to an embodiment of the present invention.
Figure 17:
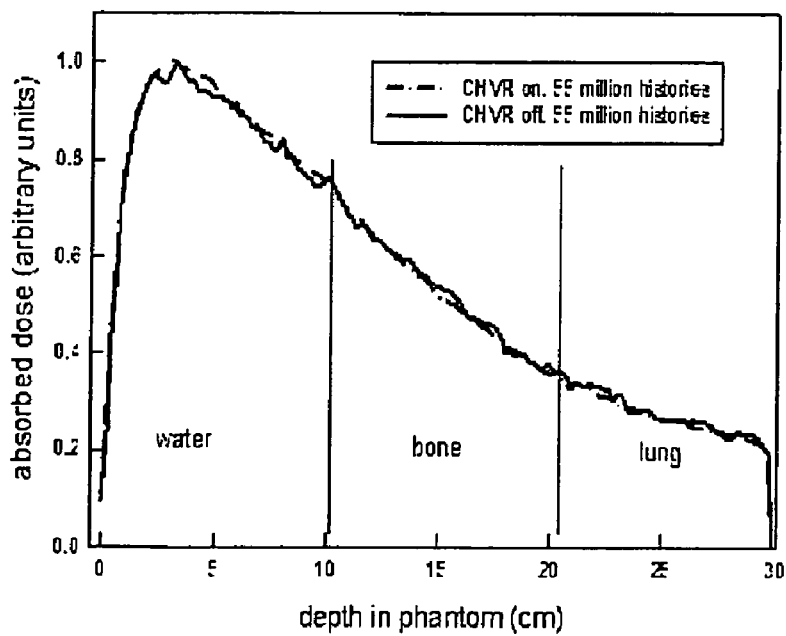
FIG. 17 is a graph of comparative depth-absorbed dose curves for a heterogeneous medium illustrating the relative effect of the relative error shown in FIG. 15 according to an embodiment of the present invention.

As noted previously, FIG. 5 illustrates that the statistical uncertainty of the calculated dose in the lung material is inherently higher than in denser materials. This results from the smaller number of scattering events in the lung, a consequence of the larger mean free path of photons or other particles. In order to compensate for this less dense material to achieve a truly constant accuracy throughout the medium, e.g., phantom or patient, more particles can be provided in less dense materials. As such, according to embodiments of the system 30, program product 71, and methods, the NVR methodology described above can also include a density correction or a density correction factor. That is, according to a first configuration, when a photon travels from a material with a density $\rho_1$ to another material with a density $\rho_2$, and if $\rho_2 < \rho_1$, instead of restoring one particle, e.g., photon, as in the original NVR, described and illustrated above, $\rho_1/\rho_2$ photons are instead restored on average. If on the other hand $\rho_2 > \rho_1$, only $\rho_1/\rho_2$ photons need be restored on average. In order to help ensure the results remain unbiased, the weight factor $W_h$ used in NVR can be multiplied by the density ratio $\rho 1/\rho 2$ or an inversely proportionally similar mean free path ratio. This modification of the NVR technique, described above, is referred to as Constant Noise Variance Reduction (CNVR) because, as shown in FIGS. 16 and 17, a constant noise (i.e., statistical uncertainty) can be achieved throughout the heterogeneous medium. Note, according to a preferred configuration of the present invention, the restoration process and weight factor calculation utilizes the ratio of photon mean free paths instead of the ratio of densities. Note also, when the ratio of $\rho_1/\rho_2$ is a fraction, an equivalent portion and equivalent portion of photons are restored according to integer values to obtain the fractional ratio. For example, if the ratio was 3.5, half of the photons encountering collisions would result in three restored virtual photons and half would result in four restored virtual photons.

As perhaps best shown in FIG. 15, in an alternative embodiment of CNVR, NVR is instead combined with and Russian roulette/particle splitting. That is, primary photons are restored when they are scattered, as described with respect to NVR. However, whenever a particle, e.g., photon, crosses a heterogeneity interface between the two types of medium, e.g., water-bone, bone-lung, the photon is Russian rouletted or split depending on whether the photon encounters a more dense material for which Russian roulette will be applied or a less dense material for which particle splitting will be applied. In this configuration, when moving away from the source and when entering less dense material, e.g., the illustrated lung material, the total number of primary photons is forced to grow to compensate for the difference in density (see FIG. 16). Note, the solid lines represent original photons and dashed lines represent restored virtual photons.

In order to help ensure the results remain unbiased, the weight factor $W_h$ used in NVR can be multiplied by the ratio of the number of photons exiting the medium type interface or boundary, after undergoing Russian roulette or particle splitting, to the number of photons entering the interface or boundary.

According to embodiments of the CNVR technique, the weight factor $W_h$ can account for the beam divergence by using an effective $\mu_i' = \mu_i + 2/r$, wherein r is the distance to the source point (not shown) in, e.g., the radiation source. Another methodology includes correcting the weight factor using the inverse square factor normalized to a reference depth.

As shown in FIGS. 15 and 16, the number of scattering events per unit volume can be kept constant (see FIG. 15), thus achieving a constant noise (i.e., accuracy) throughout the exemplary phantom (see FIG. 16). Note, FIG. 16 illustrates that at the depth d=25 cm, the relative errors for "NVR off," "NVR on," and CNVR are each ~3 percent. Neither CNVR nor NVR need to spend computing time to achieve a <3% accuracy in the depth d<25 cm region if the point of interest is at 25 cm. This recognition beneficially allows for the use of a smaller number of histories which result in the reduction in computing time and increase in efficiency of the simulation. Note further, FIG. 17 demonstrates the effectiveness of CNVR in providing unbiased results through comparison of "CNVR off" to "CNVR on" implemented with the same number of initial histories in the case of a 15 MV X-ray beam with a field size of 7 cm×7 cm irradiating a water-bone-lung phantom.

It is important to note that while embodiments of the present invention have been described in the context of a fully functional system, those skilled in the art will appreciate that the mechanism of the present invention and/or aspects thereof are capable of being distributed in the form of a computer readable medium of instructions in a variety of forms for execution on a processor, processors, or the like, and that the present invention applies equally regardless of the particular type of signal bearing media used to actually carry out the distribution. Examples of computer readable media include but are not limited to: nonvolatile, hard-coded type media such as read-only memories (ROMs), CD-ROMs, and DVD-ROMs, or erasable, electrically programmable read-only memories (EEPROMs), recordable type media such as floppy disks, hard disk drives, CD-R/RWs, DVD-RAMs, DVD-R/RWs, DVD+R/RWs, flash drives, and other newer types of memories, and transmission type media such as digital and analog communication links.

For example, such media can include both operating instructions and instructions related to the simulated dose calculation program product 71 and much of the method steps described above. For example, a computer readable medium can include a set of instructions that, when executed by one or more computers or processors, e.g., computer 61 having processors 65, cause the computer (one or more processors 65) to perform the operations of labeling separately as a primary particle each of a plurality of original primary particles from a particle beam source, e.g., radiation beam source 45, and transporting and tracking each of the plurality of original primary particles through an absorbing medium until deeming a collision event to have occurred, e.g., through statistical sampling. The instructions can also include those to perform the operations of consulting an interaction database responsive to each collision event and retrieving data on the colliding particle and each secondary particle resulting from each collision event, and recording energy deposited from each collision event to thereby build a map of absorbed dose.

The instructions can also include those to perform, in response to each collision event, the operation of creating a new virtual particle defining a restored virtual particle to artificially restore incident particle fluence, e.g., photon fluence, with depth of propagation in the medium and, at least in a homogeneous medium, to maintain statistical uncertainty of simulated absorbed dose independent of depth within the absorbing medium. The instructions can also include those to perform the operation of labeling the restored virtual photon as a primary particle and the original primary particle deemed to have collided as a scattered particle. The new virtual particle can be provided (inherits) properties from the collided original primary particle, except a new weight factor is assigned to the new virtual particle and to each scattered virtual particle to compensate for artificial constancy of the particle fluence to thereby yield unbiased results for the simulated absorbed dose. This process is then continued through a depth of interest to thereby produce a three-dimensional map of simulated absorbed dose delivered to the absorbing medium.

According to an embodiment of the present invention, for a homogeneous medium the new weight factor $W_h$ is a function of $W_{h-1} \exp(-R)$, wherein $W_{h-1}$ is the weight factor of the primary particle before the collision event, and wherein R is the radiological path length between a current location and the previous location where the primary particle was last assigned a weight factor $W_{h-1}$. Alternative ways of evaluating radiological path-length has known to those skilled in the art are within the scope of the present invention. For example, as described previously, the radiological path-length between two points where scattering events on the primary/restored particle occur can be described as the difference between the values of the pre-calculated array evaluated at those two points, e.g., $d_{eff}(I_h)-d_{eff}(I_{h-1})$.

According to an embodiment of the present invention, for a heterogeneous absorbing medium having at least two different medium types, e.g., a first medium type having a first density $\rho 1$ and associated with a first photon mean free path and a second medium type having a second density $\rho 2$ and associated with a second photon mean free path, the instructions can include those to perform the operation of restoring a number of particles on average defining restored virtual particles in response to the collision events according to a correction ratio. This ratio can be, for example, a ratio approximately equal to a ratio proportional to the first density $\rho 1$ of the first medium type to the second density $\rho 2$ of the second medium type times a Z-dependent correction factor $f(E,Z_2/Z_1)$, or a ratio proportional to the second photon mean free path to the first photon mean free path. According to this embodiment of the present invention, the weight factor $W_h$ is a function of $W_{h-1} \exp(-R)(x_2/x_1)$, wherein $W_{h-1}$ is the weight factor of the primary photon before the collision event, and wherein R is the radiological path length between a current location and the previous location where the primary photon was last assigned a weight factor $W_{h-1}$, and wherein the ratio $x_2/x_1$ is defined as one of the following: the ratio of the second density $\rho 2$ to the first density $\rho 1$ or the ratio of the first particle mean free path to the second particle mean free path. Alternative ways of evaluating radiological path-length were described previously.

As perhaps best illustrated in FIG. 15, according to an alternative embodiment of the present invention having a heterogeneous absorbing medium having at least two different medium types having interface or boundary regions between medium types, the instructions include those to perform the operations of randomly removing at least a portion of the plurality of primary particles at a removal probability when transiting between a first medium type, e.g., water, and a second medium type of a higher density, e.g., bone, and splitting each of the plurality of primary particles into a number of particles when transiting between the second medium type, e.g., bone, and a third medium type having a lower density than the second medium type, e.g., lung material. According to an embodiment of the present invention, the removal probability and the number of split particles are both proportional to a density ratio or a mean-free-path ratio across the interface. In this example, that equates to a removal probability proportional to a density ratio of the first medium type and the second medium type or mean-free-path ratio of the second medium type and the first medium type, and the number of split particles proportional to a density ratio of the first medium type and the second medium type or a mean-free-path ratio of the third medium type and the second medium type. Note, according to an embodiment of the present invention, the instructions also include those to perform the operation of adjusting a weight factor of each split primary particle to account for the beam divergence using an effective attenuation coefficient $\mu_t$, defined as $\mu_t+(2/r)$ wherein r is a distance between the collision event and beam source. Alternatively, the traditional inverse square factor can be included in order to correct for beam divergence.

This Application is related to U.S. Patent Application No. 60/691,074, filed on Jun. 16, 2005, incorporated herein by reference in its entirety.

In the drawings and specification, there have been disclosed a typical preferred embodiment of the invention, and although specific terms are employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the attached claims. For example, while the use of the NVR and CNVR has been described primarily with respect to radiation therapy planning, the foregoing systems, program product, and related methods are readily applicable to other areas including but not exclusively: nuclear reactor design and radiation shielding; x-ray imaging simulations involving low energy (KeV) photons hence large attenuations in tissue; simulation of particle deposition processes used to dope semiconductors in wafer fabrication; astronaut radiation safety considerations; simulations of earth atmosphere and space environment interactions; electronic transport in heterogeneous semiconductors especially involving electronic impact ionizations; and modeling of transportation system involving traffic jams. Further, while the use of the NVR and CNVR has been described primarily with respect to transport through a patient or a phantom, both methodologies are particularly effective in other higher density absorbing media including, for example, metals and concrete.

The invention claimed is:

1. A system for increasing efficiency in a simulation of particle transport through a medium, comprising:
   a communication network;
   an image gathering device accessible to the communication network to provide an at least two-dimensional image slice of a target volume and an adjacent structure volume in a patient;
   a radiation treatment planning computer in communication with the image gathering device and having memory, a processor coupled to the memory, and a radiation treatment planning program product stored in the memory adapted to produce an optimized radiation treatment plan for delivering radiation to the target volume;
   a radiation beam source to deliver radiation to the target according to the radiation treatment plan;
   a simulation data administrator server in communication with the communication network and having access to an interaction database including records related to parameters describing interactions of particles in an absorbing medium to provide particle interaction parameters;
   a simulated dose calculation computer in communication with the radiation treatment planning computer and the simulation data administrator server through the communication network and including memory and a plurality of processors coupled to the memory to calculate a simulated absorbed dose in the absorbing medium deliverable according to the radiation treatment plan; and
   a simulated dose calculation program product stored in the memory of the simulated dose calculation computer and including instructions that when executed by at least one of the plurality of processors causes the at least one of the plurality of processors to perform the operation of modeling the target volume and adjacent structure volume to define the absorbing medium and to perform for each of a plurality of particles deliverable from the beam source the following simulation operations:

labeling the particle as a primary particle responsive to initiating a radiation delivery simulation through the absorbing medium according to the radiation treatment plan, transporting the primary particle through the absorbing medium, tracking the primary particle through the absorbing medium until undergoing a scattering event, determining the scattering event to have occurred, the scattering event resulting in a change in incident particle fluence with depth of propagation in the absorbing medium, consulting the interaction database responsive to the scattering event and retrieving data on the primary particle and any secondary particles resulting from the scattering event when so existing, recording energy deposited from the scattering event to thereby build a map of simulated absorbed dose, creating a new virtual particle defining a restored virtual particle responsive to the scattering event to thereby artificially restore incident particle fluence with depth of propagation in the absorbing medium changed in response to the scattering event, inheriting by the restored virtual particle properties from the primary particle, labeling the restored virtual particle as a primary particle and the original primary particle determined to have scattered as a scattered particle responsive to the scattering event, assigning a weight factor to each scattered virtual particle to compensate for artificial constancy of the particle fluence to thereby yield unbiased results for the simulated absorbed dose, and producing a three-dimensional map of simulated absorbed dose delivered to the absorbing medium.

2. A system as defined in claim 1, wherein the simulated dose calculation program product further includes instructions to perform the operation of assigning the same weight factor to each virtual particle resulting from the scattering event to compensate for the artificial constancy of the particle fluence resulting from the artificial restoration of incident particle fluence to thereby yield unbiased results for the simulated absorbed dose.

3. A system as defined in claim 2, wherein the weight factor is defined as $W_h = W_{h-1} \exp(-\Sigma \mu_i z_i)$, wherein $W_{h-i}$ is a weight factor of the primary particle before the scattering event, wherein $z_i$ is a step length, wherein $\mu_i$ is an attenuation coefficient within each step length $z_i$, and wherein $\Sigma \mu_i z_i$ represents the radiological path length between a current location and the previous location where the primary particle was last assigned the weight factor $W_{h-1}$.

4. A system as defined in claim 2, wherein the weight factor is defined as $W_h = W_{h-1} \exp(-(d_{eff}(I_h) - d_{eff}(I_{h-1})))$, wherein $W_{h-1}$ is a weight factor of the primary particle before the scattering event, wherein I identifies a given voxel, wherein $d_{eff}(I)$ represents a precalculated voxel-dependent array of radiological path lengths, and wherein $d_{eff}(I_h) - d_{eff}(I_{h-1})$ represents the radiological path length between a current location and the previous location where the primary particle was last assigned the weight factor $W_{H-1}$.

5. A system as defined in claim 1, wherein the simulated dose calculation program product further includes instructions to perform the operation of assigning the restored virtual particle a new weight factor according to an attenuation coefficient responsive to creating the restored virtual particle.

6. A system as defined in claim 5, wherein the restored virtual particle inherits all properties of the primary particle except for the assigned new weight factor.

7. A system as defined in claim 1, wherein the scattering event includes one of the following: Compton scattering, pair production, photo-electric effect, coherent scattering, elastic interactions, nuclear excitation, nuclear reactions, and neutron decay.

8. A system as defined in claim 1, wherein the instructions further include those to perform the operation of not restoring scattered particles in further scattering events.

9. A system as defined in claim 1, wherein the absorbing medium is heterogeneous having at least two different medium types, a first medium type having a first density $\rho 1$ and associated with a first particle mean free path, and a second medium type having a second density $\rho 2$ and associated with a second particle mean free path, and wherein the simulated dose calculation program product further includes instructions to perform the operations of:

restoring a number of primary particles responsive to the scattering event for each of the plurality of primary particles; and scaling the number of restored particles according to a ratio approximately equal to one of the following: a ratio of the first density pi of the first medium type to the second density $\rho 2$ of the second medium type, a ratio of the first density $\rho 1$ of the first medium type to the second density $\rho 2$ of the second medium type times a factor dependent on a ratio of atomic numbers for the first and the second medium types when the ratio of atomic numbers is different from unity, and a ratio of the second particle mean free path to the first particle mean free path.

10. A system as defined in claim 9, wherein the simulated dose calculation program product further includes instructions to perform the operation of assigning each restored virtual particle a new weight factor $W_h$ responsive to creating the restored virtual particle, wherein the weight factor is defined as $W_h = W_{h-1} \exp(-\Sigma \mu_i z_i)(x_2/x_1)$, wherein $W_{h-1}$ is a weight factor of the primary particle before the scattering event, wherein $z_i$, is a step length, wherein $\mu_i$ is an attenuation coefficient within each step length $z_i$ and wherein $\Sigma \mu_i z_i$ represents the radiological path length between a current location and the previous location where the primary particle was last assigned the weight factor $W_{h-1}$, and wherein the ratio $x_2/x_1$ is defined as one of the following: a ratio of the second density $\rho 2$ to the first density $\rho 1$, a ratio of the second density $\rho 2$ to the first density $\rho 1$ times a factor dependent on the ratio of atomic numbers for the second and the first medium types when the ratio of atomic numbers is different from unity, and a ratio of the first particle mean free path to the second particle mean free path.

11. A system as defined in claim 9, wherein the simulated dose calculation program product further includes instructions to perform the operation of assigning each restored virtual particle a new weight factor $W_h$ responsive to creating the restored virtual particle, wherein the weight factor is defined as $Wh = W_{h-1} \exp(-R)(x_2/x_1)$, wherein $W_{h-1}$ is a weight factor of the primary particle before the scattering event, and wherein R represents the radiological path length between a current location and the previous location where the primary particle was last assigned the weight factor $W_{h-1}$ and wherein the ratio $X_2/X_1$ is defined as one of the following: a ratio of the second density $\rho 2$ to the first density $\rho 1$, a ratio of the second density ρ2 to the first density ρ1 times a factor dependent on the ratio of atomic numbers for the second and the first medium types when the ratio of atomic numbers is substantially different from unity, and the ratio of the first particle mean free path to the second particle mean free path.

12. A system as defined in claim 11, wherein $R=d_{eff}(I_h)-d_{eff}(I_{h-1})$, wherein I identifies a given voxel, and wherein $d_{eff}(I)$ represents a precalculated voxel-dependent array of radiological path lengths.

13. A system as defined in claim 1, wherein the absorbing medium is heterogeneous having at least two different medium types, and wherein the simulated dose calculation program product further includes instructions to perform at least one of the following operations:
- splitting each one of the plurality of primary particles into a number of particles responsive to each one of the plurality of primary particles passing an interface between a first medium type and a second medium type having a lower density than the first medium type, the number of split primary particles proportional to a density ratio times a factor dependent on a ratio of atomic numbers for the first and the second medium types when the ratio of atomic numbers is different from unity, or a mean-free-path ratio of the second medium type and the first medium type; and
- randomly removing a subset of the plurality of primary particles at a removal probability responsive to the plurality of primary particles passing an interface between a third medium type and a fourth medium type having a higher density than the third medium type, the removal probability proportional to a density ratio times a factor dependent on a ratio of atomic numbers for the third and the fourth medium types when the ratio of atomic numbers is different from unity, or a mean-free-path ratio of the fourth medium type and the third medium type.

14. A system for increasing efficiency in a simulation of particle transport through a medium, comprising:
- a simulated dose calculation computer including memory and at least one processor coupled to the memory to calculate a simulated absorbed dose in an absorbing medium; and
- a simulated dose calculation program product stored in the memory of the simulated dose calculation computer and including instructions that when executed by the at least one processor causes the at least one processor to perform the following simulation operations:
  - labeling a particle as a primary particle responsive to initiating a radiation delivery simulation,
  - creating a new virtual particle defining a restored virtual particle responsive to a collision event involving the primary particle, labeling the restored virtual particle as a primary particle and the original primary particle as a scattered particle responsive to the collision event; and
  - restoring incident particle fluence with depth of propagation in the absorbing medium changed in response to the collision event.

15. A system as defined in claim 14, wherein the simulated dose calculation program product further includes instructions to perform the operation of assigning a weight factor to each scattered virtual particle to compensate for artificial constancy of the particle fluence to thereby yield unbiased results for the simulated absorbed dose.

16. A system as defined in claim 15, wherein the simulated dose calculation program product further includes instructions to perform the operation of assigning a weight factor to each restored virtual particle resulting from the collision event to compensate for the artificial constancy of the particle fluence to thereby yield unbiased results for the simulated absorbed dose.

17. A system as defined in claim 16, wherein the weight factor is defined as $W_h=W_{h-1} \exp(-d_{eff}(I_h)-d_{eff}(I_{h-1})))$, wherein $W_{h-1}$ is a weight factor of the primary particle before the scattering event, wherein I identifies a given voxel, wherein $d_{eff}(I)$ represents a precalculated voxel-dependent array of radiological path lengths, and wherein $d_{eff}(I_h)-d_{eff}(I_{h-1})$ represents the radiological path length between a current location and the previous location where the primary particle was last assigned the weight factor $W_{h-1}$.

18. A system as defined in claim 17, wherein the restored virtual particle inherits all properties of the primary particle except for the assigned new weight factor.

19. A system as defined in claim 14, wherein the collision event includes one of the following: Compton scattering, pair production, photo-electric effect, and coherent scattering, elastic interactions, nuclear excitation, nuclear reactions, and neutron decay.

20. A system as defined in claim 14, wherein the instructions further include those to perform the operation of not restoring scattered particles in further collision events.

21. A system as defined in claim 14,
- wherein the absorbing medium is heterogeneous having at least two different medium types, a first medium type having a first density ρ1 and associated with a first particle mean free path, and a second medium type having a second density ρ2 and associated with a second particle mean free path;
- wherein the restoration operation is performed on each of a plurality of primary particles each experiencing a collision; and
- wherein the simulated dose calculation program product further includes instructions to perform the operation of restoring a number of particles on average defining restored virtual particles responsive to the collision events according to a ratio approximately equal to one of the following: a ratio of the first density ρ1 of the first medium type to the second density ρ2 of the second medium type, a ratio of the first density ρ1 of the first medium type to the second density ρ2 of the second medium type times a factor dependent on a ratio of atomic numbers for the first and the second medium types when the ratio of atomic numbers is different from unity, and a ratio of the second particle mean free path to the first particle mean free path.

22. A system as defined in claim 21, wherein the simulated dose calculation program product further includes instructions to perform the operation of assigning each restored virtual particle a new weight factor $W_h$, responsive to creating the restored virtual particle, wherein the weight factor is defined as $Wh=Wh-1 \exp(-\Sigma\mu_i z_i)(x_2/x_1)$,
- wherein $W_{h-1}$ is a weight factor of the primary particle before the collision event, wherein $z_i$ is a step length, wherein $\mu_i$ is an attenuation coefficient within each step length $z_i$, and wherein $\Sigma\mu_i z_i$ is the radiological path length between a current location and the previous location where the primary particle was last assigned a weight factor $W_{h-i}$, and wherein the ratio $x_2/x_1$ is defined as one of the following: the ratio of the second density ρ2 of the second medium type to the first density ρ1 of the first medium type, the ratio of the second density ρ2 to the first density ρ1 times the factor dependent on the ratio of atomic numbers for the first and the second medium types when the ratio of atomic numbers is different from unity, and the ratio of the first particle mean free path to the second particle mean free path.

23. A system as defined in claim 21, wherein the simulated dose calculation program product further includes instructions to perform the operation of assigning each restored virtual particle a new weight factor $W_h$, responsive to creating the restored virtual particle, wherein the weight factor is defined as $W_h = W_{h-1} \exp(-R)(x_2/x_1)$, wherein R is the radiological path length between a current location and the previous location where the primary particle was last assigned a weight factor $W_{h-1}$ and wherein the ratio $x_2/x_1$ is defined as one of the following: the ratio of the second density $\rho 2$ of the second medium type to the first density $\rho 1$ of the first medium type, the ratio of the second density $\rho 2$ to the first density pi times the factor dependent on the ratio of atomic numbers for the first and the second medium types when the ratio of atomic numbers is different from unity, and the ratio of the first particle mean free path to the second particle mean free path.

24. A system as defined in claim 14, wherein the absorbing medium is heterogeneous having at least two different medium types, wherein a plurality of primary particles is transported through the absorbing medium, and wherein the simulated dose calculation program product further includes instructions to perform at least one of the following operations:
   randomly removing at least a portion of the plurality of primary particles at a removal probability responsive to the plurality of primary particles passing an interface between a first medium type and a second medium type having a higher density than the first medium type, the removal probability proportional to a density ratio times a ratio of atomic numbers for the first medium type and the second medium type when the ratio of atomic numbers is different from unity, or a mean-free-path ratio of the second medium type and the first medium type; and
   splitting each of the plurality of primary particles into a number of particles responsive to passing an interface between a third medium type and a fourth medium type having a lower density than the third medium type, the number of split primary particles proportional to a density ratio times a ratio of atomic numbers for the third medium type and the fourth medium type when the ratio of atomic numbers is different from unity, or a mean-free-path ratio of the fourth medium type and the third medium type.

25. A method of increasing efficiency in a simulation of particle transport device through a non-transitory computer readable medium, comprising the steps of:
   selecting an original particle from a radiation source;
   tracking the selected original particle through a medium until undergoing a collision event, the collision event resulting in a change in incident particle fluence with depth of propagation in the medium;
   consulting an interaction database responsive to the collision event;
   retrieving data on the original particle and each secondary particle resulting from the collision event;
   recording energy deposited from the collision event; and
   creating a new virtual particle defining a restored virtual particle responsive to the collision event to thereby artificially restore incident particle fluence with depth of propagation in the medium changed in response to the collision event.

26. The method of increasing efficiency in said simulation of particle transport device through said non-transitory computer readable medium as defined in claim 25, wherein both the original particle and the restored virtual particle are primary particles, and wherein the method further comprises:
   inheriting by the restored virtual particle all properties of the original particle except for an assigned new weight factor; and
   labeling the restored virtual particle as a primary particle and the original primary particle determined to have collided as a scattered particle responsive to the collision event.

27. The method of increasing efficiency in said simulation of particle transport device through said non-transitory computer readable medium as defined in claim 25, wherein the collision event results in at least one scattered virtual particle, and wherein the method further comprises the steps of:
   assigning weight factors to each scattered virtual particle to compensate for artificial constancy of the particle fluence to thereby yield unbiased results for a simulated absorbed dose; and
   producing a three-dimensional map of simulated radiation dose delivered to the medium.

28. The method of increasing efficiency in said simulation of particle transport device through said non-transitory computer readable medium as defined in claim 25 further comprising the step of assigning the restored virtual particle a new weight factor.

29. A method of increasing efficiency in a simulation of particle transport device through a non transitory computer readable medium by reducing a number of required particles to be tracked, the method comprising the steps of:
   labeling each of a plurality of original primary particles from a particle beam source separately as a primary particle;
   transporting each of the plurality of original primary particles through an absorbing medium;
   creating a new virtual particle defining a restored virtual particle responsive to a collision event of one of the plurality of original primary particles;
   inheriting properties by the restored virtual particle from the collided original primary particle; and
   labeling the restored virtual particle as a primary particle and the original primary particle as a scattered particle responsive to the collision event.

30. The method of increasing efficiency in said simulation of particle transport device through the non transitory computer readable medium by reducing said number of required particles to be tracked as defined in claim 29, further comprising the step of maintaining statistical uncertainty of simulated absorbed dose independent of depth within the absorbing medium.

31. The method of increasing efficiency in said simulation of particle transport device through the non transitory computer readable medium by reducing said number of required particles to be tracked as defined in claim 29, further comprising the step of maintaining primary particle fluence invariant with the depth of the absorbing medium.

32. The method of increasing efficiency in said simulation of particle transport device through the non transitory computer readable medium by reducing said number of required particles to be tracked as defined in claim 29, wherein the absorbing medium is heterogeneous having at least two different medium types, a first medium type having a first density $\rho 1$ and associated with a first particle mean free path, and a second medium type having a second density $\rho 2$ and associated with a second particle mean free path, wherein the step of creating a restored virtual particle is performed for a plurality of original primary particles and a plurality of restored particles each encountering a collision event in the second medium type at a rate approximately proportional to one of the following: a ratio of the first density ρ1 of the first medium type to the second density ρ2 of the second medium type, a ratio of the first density ρ1 to the second density ρ2 times a factor dependent on the ratio of atomic numbers for the first and the second medium types when the ratio of atomic numbers is different from unity, and a ratio of the second particle mean free path to the first particle mean free path.

33. The method of increasing efficiency in said simulation of particle transport device through the non transitory computer readable medium by reducing said number of required particles to be tracked as defined in claim 32, further comprising the step of assigning each restored virtual particle a new weight factor $W_h$ responsive to creating the restored virtual particle, wherein the weight factor $W_h$ is defined as $W_{h-1} \exp(-\Sigma \mu_i z_i)(x_2/x_1)$, wherein $W_{h-1}$ is the weight factor of the primary particle before the collision event, wherein $z_i$, is a step length, wherein $\mu_i$ is an attenuation coefficient within each step length $z_i$ wherein $\Sigma \mu_i z_i$, represents the radiological path length between a current location and the previous location where the primary particle was last assigned a weight factor $W_{h-1}$ and wherein the ratio $x_2/x_1$ is defined as one of the following: the ratio of the first density ρ1 of the first medium type to the second density ρ2 of the second medium type, the ratio of the first density ρ1 to the second density ρ2 times the factor dependent on the ratio of atomic numbers for the first and the second medium types when the ratio of atomic numbers is different from unity and the ratio of the second particle mean free path to the first particle mean free path.

34. The method of increasing efficiency in said simulation of particle transport device through the non transitory computer readable medium by reducing said number of required particles to be tracked as defined in claim 32, further comprising the step of assigning each restored virtual particle a new weight factor $W_h$, responsive to creating the restored virtual particle, wherein the weight factor $W_h$ is defined as $W_{h-1} \exp(-d_{\mathit{eff}}(I_h)-d_{\mathit{eff}}(I_{h-1})) (x_2/x_1)$, wherein I identifies a given voxel, wherein $d_{\mathit{eff}}(I)$ represents a precalculated voxel-dependent array of radiological path lengths, wherein $d_{\mathit{eff}}(I_h)-d_{\mathit{eff}}(I_{h-1})$ represents the radiological path length between a current location and the previous location where the primary particle was last assigned a weight factor $W_{h-1}$ and wherein the ratio $x_2/x_1$ is defined as one of the following: the ratio of the first density ρ1 to the second density ρ2, the ratio of the first density ρ1 to the second density ρ2 times the factor dependent on the ratio of atomic numbers for the first and the second medium types when the ratio of atomic numbers is different from unity, and the ratio of the second particle mean free path to the first particle mean free path.

35. The method of increasing efficiency in said simulation of particle transport device through said non transitory computer readable medium by reducing said number of required particles to be tracked as defined in claim 29, wherein the absorbing medium is heterogeneous having at least two different medium types, the method further comprising performing at least one of the following steps to maintain substantially constant a number of collision events per unit volume throughout the absorbing medium;
splitting at least one of the plurality of primary particles into a number of particles responsive to the at least one of the plurality of primary particles passing an interface between a first medium type and a second medium type having a lower density than the first medium type to compensate for beam divergence inherent in lower density material to thereby maintain approximately constant a number of collision events per unit volume, the number of split primary particles proportional to a density ratio times a ratio of atomic numbers for the first and the second medium types when the ratio of atomic numbers is different from unity, or a mean-free-path ratio of the second medium type and the first medium type; and
randomly removing at least one of the plurality of primary particles at a removal probability responsive to the at least one of the plurality of primary particles passing an interface between a third medium type and a fourth medium type having a higher density than the third medium type, the removal probability proportional to a density ratio times a ratio of atomic numbers for the third and the fourth medium types when the ratio of atomic numbers is different from unity, or a mean-free-path ratio of the fourth medium type and the third medium type.

36. A method to increase efficiency of Monte Carlo simulations on a non-transitory computer readable medium to control a particle transport device or radiation fluxes, comprising the steps of:
providing parameters for a medium to perform a Monte Carlo simulation thereon;
artificially adjusting simulation particle fluxes to achieve a substantially constant accuracy throughout a depth of the medium;
wherein the step of artificially adjusting the simulation particle fluxes is achieved by:
restoring a particle when the particle is absorbed or scattered; and
assigning the restored particle a weight factor according to an attenuation coefficient and particle mean free path of the restored particle to thereby achieve unbiased final simulation results.

37. The method to increase efficiency of Monte Carlo simulations on said non-transitory computer readable medium to control said particle transport device or radiation fluxes of claim 36, wherein the medium includes two medium types, and wherein the step of artificially adjusting the simulation particle fluxes is achieved by at least one of the following:
restoring for each of a plurality of original particles a number of particles defining restored particles when an original particle transported through the medium is determined to be absorbed or scattered defining a collision event, scaling the number of restored particles according to a mean free path of the original particle associated with the medium at a location of the collision event, and assigning each restored particles a weight factor to thereby achieve unbiased final simulation results; and
restoring an original particle according to a probability, the probability corresponding to a density ratio for the two medium types, the density ratio times a ratio of the atomic numbers for the two medium types, or a mean free path ratio for the two medium types.

38. The method to increase efficiency of Monte Carlo simulations on said non-transitory computer readable medium to control said particle transport device or radiation fluxes of claim 36, wherein the medium includes a plurality of medium types, and wherein the step of artificially adjusting the simulation particle fluxes is achieved by;
splitting a particle to a number of particles responsive to the particle passing an interface between a first medium type and a second medium type having a lower density than the first medium type, the number of split particles proportional to a density ratio times a correction factor, or a mean-free-path ratio of the second medium type and the first medium type; and randomly removing the particle at a removal probability responsive to the particle passing an interface between a third medium type and a fourth medium type having a higher density than the third medium type, the removal probability proportional to a density ratio times a correction factor, or a mean-free-path ratio of the fourth medium type and the third medium type.

39. A non-transitory computer readable medium that is readable by at least one computer processor, the computer readable medium comprising a set of instructions that, when executed by the at least one computer processor, cause the at least one computer processor to perform the following operations:
  selecting a particle from a radiation source;
  tracking the selected particle through a medium until undergoing a collision event, the collision event resulting in a change in incident particle fluence with depth of propagation in the medium;
  consulting an interaction database responsive to the collision event;
  retrieving data on the particle and each secondary particle resulting from the collision event;
  recording energy deposited from the collision event; and
  creating a new virtual particle defining a restored virtual particle responsive to the collision event to thereby artificially restore incident particle fluence with depth of propagation in the medium changed in response to the collision event.

40. The non-transitory computer readable medium as defined in claim 39, wherein the particle is a primary particle, and wherein the restored virtual particle inherits all properties of the primary particle except for an assigned new weight factor.

41. The non-transitory computer readable medium as defined in claim 39, wherein the collision event results in at least one scattered virtual particle, and wherein the instructions further include those to perform the operations of:
  assigning weight factors to each scattered virtual particle to compensate for artificial constancy of the particle fluence to thereby yield unbiased results for a simulated absorbed dose; and
  producing a three-dimensional map of simulated radiation dose delivered to the medium responsive to the recorded energy from the collision event.

42. The non-transitory computer readable medium as defined in claim 41, wherein the instructions further include those to perform the operation of assigning the restored virtual particle a new weight factor.

43. A non-transitory computer readable medium that is readable by at least one computer processor, the computer readable medium comprising a set of instructions that, when executed by the at least one computer processor, cause the at least one computer processor to perform the following operations:
  creating a new virtual particle defining a restored virtual particle responsive to a collision event, the collision event resulting in a change in incident particle fluence with depth of propagation in a medium;
  labeling the restored virtual particle as a primary particle and an original primary particle determined to have collided as a scattered particle responsive to the collision event; and
  restoring incident particle fluence with depth of propagation in the medium changed in response to the collision event.

44. The non-transitory computer readable medium as defined in claim 43, wherein the instructions further include those to perform the operation of assigning a weight factor to each scattered virtual particle to compensate for artificial constancy of the particle fluence to thereby yield unbiased results for calculating simulated absorbed dose.

45. The non-transitory computer readable medium as defined in claim 44, wherein the instructions further include those to perform the operation of assigning a weight factor to each restored virtual particle resulting from the collision event to compensate for the artificial constancy of the particle fluence to thereby yield unbiased results for calculating the simulated absorbed dose.

46. The non-transitory computer readable medium as defined in claim 44, wherein the weight factor is defined as $W_h = W_{h-1} \exp(-\Sigma \mu_i z_i)$, wherein $W_{h-1}$ is the weight factor of the primary particle before the collision event, wherein $z_i$ is a step length, wherein $\mu_i$ is an attenuation coefficient within each step length $z_i$, and wherein $\Sigma \mu_i z_i$ represents the radiological path length between a current location and the previous location where the primary particle was last assigned a weight factor.

47. The non-transitory computer readable medium as defined in claim 44, wherein the weight factor is defined as $W_h = W_{h-1} \exp(-d_{eff}(I_h) - d_{eff}(I_{h-1}))$, wherein $W_{h-1}$ is a weight factor of the primary particle before the scattering event, wherein I identifies a given voxel, wherein $d_{eff}(I)$ represents a precalculated voxel-dependent array of radiological path lengths, and wherein $(d_{eff}(I_h) - d_{eff}(I_{h-1}))$ is the radiological path length between a current location and the previous location where the primary particle was last assigned the weight factor $W_{h-1}$.

48. The non-transitory computer readable medium as defined in claim 47, wherein the restored virtual particle inherits all properties of the collided primary particle except for the assigned weight factor.

49. The non-transitory computer readable medium as defined in claim 43,
  wherein the medium is heterogeneous having at least two different medium types, a first medium type having a first density $\rho 1$ and associated with a first particle mean free path, and a second medium type having a second density $\rho 2$ and associated with a second particle mean free path;
  wherein the restoration operation is performed on each of a plurality of primary particles each experiencing a collision; and
  wherein the instructions include those to perform the operation of restoring a number of particles on average defining restored virtual particles responsive to the collision events according to a ratio approximately equal to at least one of the following: a ratio of the first density $\rho 1$ of the first medium type to the second density $\rho 2$ of the second medium type, a ratio of the first density $\rho 1$ of the first medium type to the second density $\rho 2$ of the second medium type times a correction factor when a ratio of average atomic numbers for the first and the second medium types is different from unity, and a ratio of the second particle mean free path to the first particle mean free path.

50. The non-transitory computer readable medium as defined in claim 49, wherein the instructions include those to perform the operation of assigning each restored virtual particle a new weight factor $W_h$ responsive to creating the restored virtual particle, wherein the weight factor is defined as $W_h = W_{h-1} \exp(-\Sigma \mu_i z_i)(x_2/x_1)$, wherein $W_{h-1}$ is the weight factor of the primary particle before the collision event, wherein $z_i$, is a step length, wherein $\mu_i$ is an attenuation coefficient within each step length $z_i$ and wherein $\Sigma \mu_i z_i$ is the radiological path length between a current location and the previous location where the primary particle was last assigned a weight factor $W_{h-1}$ and wherein the ratio $x_2/x_1$ is defined as one of the following: the ratio of the second density $\rho 2$ of the second medium type to the first density $\rho 1$ of the first medium type, the ratio of the second density $\rho 2$ to the first density $\rho 1$ type times a correction factor when a ratio of average atomic numbers for the first and the second medium types is different from unity, and the ratio of the first particle mean free path to the second particle mean free path.

51. The non-transitory computer readable medium as defined in claim 49, wherein the instructions include those to perform the operation of assigning each restored virtual particle a new weight factor $W_h$ responsive to creating the restored virtual particle, wherein the weight factor $W_h$ is defined as $W_{h-1} \exp(-d_{\it{eff}}(I_h)-d_{\it{eff}}(I_{h-1})(x_2/x_1))$, wherein $W_{h-1}$ is the weight factor of the primary particle before the collision event, wherein I identifies a given voxel, wherein $d_{\it{eff}}(I)$ represents a precalculated voxel-dependent array of radiological path lengths, wherein $(d_{\it{eff}}(I_h)-d_{\it{eff}}(I_{h-1}))$ is the radiological path length between a current location and the previous location where the primary particle was last assigned a weight factor $W_{h-1}$ and wherein the ratio $x_2/x_1$ is defined as one of the following: the ratio of the second density $\rho 2$ of the second medium type to the first density $\rho 1$ of the first medium type, the ratio of the second density $\rho 2$ to the first density $\rho 1$ times a correction factor when a ratio of average atomic numbers for the first and the second medium types is different from unity, and the ratio of the first particle mean free path to the second particle mean free path.

52. The non-transitory computer readable medium as defined in claim 43, wherein the medium is heterogeneous having at least two different medium types, wherein a plurality of primary particles is transported through the medium, and wherein the instructions include those to perform at least one of the following operations:
    randomly removing at least a portion of the plurality of primary particles at a removal probability responsive to the plurality of primary particles passing an interface between a first medium type and a second medium type having a higher density than the first medium type, the removal probability proportional to a density ratio times a correction factor when a ratio of average atomic numbers for the first and the second medium types is different from unity, or a mean-free-path ratio of the second medium type and the first medium type; and
    splitting each of the plurality of primary particles into a number of particles responsive to passing an interface between a third medium type and a fourth medium type having a lower density than the third medium type, the number of split primary particles proportional to a density ratio times a correction factor when a ratio of average atomic numbers for the third and the fourth medium types is different from unity, or a mean-free-path ratio of the fourth medium type and the third medium type.

53. A non-transitory computer readable medium that is readable by at least one computer processor, the computer readable medium comprising a set of instructions that, when executed by the at least one computer processor, cause the at least one computer processor to perform the following operations:
    providing parameters for a medium to perform a Monte Carlo simulation thereon;
    artificially adjusting simulation particle fluxes to achieve a substantially constant variance throughout a depth of the medium;
    wherein the operation of artificially adjusting the simulation particle fluxes is achieved by:
    restoring a particle when the particle is absorbed or scattered; and
    assigning the restored particle a weight factor according to an attenuation coefficient particle mean free path of the restored particle to thereby achieve unbiased simulation final results.

54. The non-transitory computer readable medium of claim 53, wherein the medium includes two medium types, and wherein the operation of artificially adjusting the simulation particle fluxes is achieved by at least one of the following:
    restoring for each of a plurality of original particles a number of particles defining restored particles when an original particle transported through the medium is absorbed or scattered defining a collision event;
scaling the number of restored particles according to a mean free path of the original particle associated with the medium at a location of the collision event; and assigning each restored particle a weight factor to thereby achieve unbiased simulation final results; and
    restoring an original particle according to a probability, the probability corresponding to a density ratio for the two medium types, the density ratio times a ratio of the atomic numbers for the two medium types, or a mean free path ratio for the two medium types.

* * * * *